United States Patent
Han et al.

(10) Patent No.: US 12,370,161 B2
(45) Date of Patent: Jul. 29, 2025

(54) COMPOSITION FOR TREATING ATOPY OR PRURITUS COMPRISING N-ACETYL OR N-ACYL AMINO ACID

(71) Applicants: STEMDR INC., Jeollabuk-do (KR); INDUSTRIAL COOPERATION FOUNDATION CHONBUK NATIONAL UNIVERSITY, Jeollabuk-do (KR); KOREA RESEARCH INSTITUTE OF CHEMICAL TECHNOLOGY, Daejeon (KR)

(72) Inventors: Myung-Kwan Han, Jeollabuk-do (KR); Kwangho Lee, Daejeon (KR)

(73) Assignees: STEMDR INC., Jeollabuk-do (KR); INDUSTRIAL COOPERATION FOUNDATION CHONBUK NATIONAL UNIVERSITY, Jeollabuk-do (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 17/668,678

(22) Filed: Feb. 10, 2022

(65) Prior Publication Data
US 2022/0233485 A1 Jul. 28, 2022

Related U.S. Application Data

(62) Division of application No. 16/766,891, filed as application No. PCT/KR2018/014483 on Nov. 23, 2018, now abandoned.

(30) Foreign Application Priority Data

Nov. 24, 2017 (KR) .................. 10-2017-0158599
Nov. 22, 2018 (KR) .................. 10-2018-0145159

(51) Int. Cl.
| | | |
|---|---|---|
| A61K 31/198 | (2006.01) | |
| A23L 33/00 | (2016.01) | |
| A23L 33/175 | (2016.01) | |
| A61K 8/02 | (2006.01) | |
| A61K 8/44 | (2006.01) | |
| A61K 8/49 | (2006.01) | |
| A61K 31/405 | (2006.01) | |
| A61P 17/04 | (2006.01) | |
| A61Q 19/00 | (2006.01) | |

(52) U.S. Cl.
CPC .......... *A61K 31/198* (2013.01); *A23L 33/175* (2016.08); *A23L 33/40* (2016.08); *A61K 8/0212* (2013.01); *A61K 8/442* (2013.01); *A61K 8/4913* (2013.01); *A61K 31/405* (2013.01); *A61P 17/04* (2018.01); *A61Q 19/007* (2013.01); *A23V 2002/00* (2013.01)

(58) Field of Classification Search
CPC ......... A61P 17/04; A61P 17/00; A61P 29/00; A61P 9/00; A61P 35/00; A61P 37/00; A61P 11/00; A61P 11/06; A61P 17/02; A61P 19/02; A61P 21/00; A61P 25/00; A61P 25/24; A61P 25/28; A61P 31/14; A61P 35/02; A61P 37/08; A61P 43/00; A61P 9/06; A61P 17/18; A61Q 19/00; A61Q 19/007; A61Q 17/04
See application file for complete search history.

(56) References Cited

U.S. PATENT DOCUMENTS

| | | | |
|---|---|---|---|
| 3,971,701 A | | 7/1976 | Takinami |
| 6,159,485 A | * | 12/2000 | Yu ................. A61K 31/401 |
| | | | 514/20.7 |
| 2003/0185864 A1 | | 10/2003 | Kobayashi |
| 2005/0171194 A1 | | 8/2005 | Yu |
| 2006/0034781 A1 | | 2/2006 | Takahashi |
| 2006/0063827 A1 | | 3/2006 | Yu |
| 2007/0099888 A1 | | 5/2007 | Iwasaki |
| 2010/0292313 A1 | | 11/2010 | Baguisi |

FOREIGN PATENT DOCUMENTS

| | | | |
|---|---|---|---|
| GB | 2052985 | 2/1981 | |
| JP | H03251562 | 11/1991 | |
| JP | H08053332 | 2/1996 | |
| JP | H09505823 | * 6/1997 | .......... A61Q 19/007 |

(Continued)

OTHER PUBLICATIONS

Lough et al. ("Assessment of chiral stationary phases for suitability for combined enantiomeric impurity/related substances assays", available online Oct. 10, 2011, Journal of Chromatography A, 1218, (2011), 8655-8663). (Year: 2011).*
JPH09505823 translation, Beiersdorf AG Assignee, published Jun. 1997, machine translation (Year: 1997).*
Andersen et al., "Human Surrogate Models of Histaminergic and Non-histaminergic Itch", Acta Derm Venereol, vol. 95, May 2015, pp. 771-777.
Sano et al., "Thymic stromal lymphoietin expression is increased in the horny later of patients with atopic dermatitis", British Society for Immunology, Clinical and Experimental Immunology, vol. 171, 2012, pp. 330-337.

(Continued)

*Primary Examiner* — Audrea B Coniglio
(74) *Attorney, Agent, or Firm* — DUANE MORRIS LLP; Gregory M. Lefkowitz; Brandon A. Chan

(57) ABSTRACT

The present disclosure relates to a composition for preventing, alleviating or treating pruritus and/or atopy using an N-acetylamino acid or an N-acylamino acid having almost no side effects on the human body. Also, the present disclosure relates to a cosmetic composition for moisturizing skin or soothing skin. The composition of the present disclosure may be utilized to ameliorate a problematic skin condition caused by various causes, or to safely and effectively alleviate or treat pruritus and/or atopy without concern about side effects.

5 Claims, 15 Drawing Sheets

(56) References Cited

FOREIGN PATENT DOCUMENTS

| JP | 2001-213754 | 7/2001 | | |
|---|---|---|---|---|
| JP | 2002-534369 | 10/2002 | | |
| JP | 2006-327972 | 12/2006 | | |
| KR | 10-2005-0072118 | 7/2005 | | |
| KR | 10-2016-0025951 | 9/2016 | | |
| WO | 2000040217 | 7/2000 | | |
| WO | 2010/062502 | 6/2010 | | |
| WO | WO2010/075891 A1 * | 7/2010 | ............. | A61K 39/00 |
| WO | WO2013/040441 A1 * | 3/2013 | ........... | A61K 31/573 |

OTHER PUBLICATIONS

Vos et al., "Years lived with disability (YLDs) for 1160 sequelae of 289 diseases and injuries 1990-2010: a systematic analysis for the Global Burden of Disease Study 2010", Lancet, vol. 380, No. 9859, Dec. 2012, pp. 2163-2196.

Wilson et al., "The Epithelial Cell-derived Atopic Dermatitis Cytokine TSLP Activates Neurons to Induce Itch", Cell, vol. 155, No. 2, Oct. 2013, pp. 285-295.

Ziegler et al., "Thymic stromal lymphopoietin in normal and pathogenic T cell development and function", Nature Immunology, vol. 7, No. 7, Jul. 2006, pp. 709714.

Burnett, C.L., "Safety Assessment of Amino Acid Alkyl Amides as Used in Cosmetics," International Journal of Toxicology, 2017, vol. 36 (Supplement I).

Sekine, S., et al., "Handbook of Cosmetics—New Edition," Chuo Printing Co., Ltd., Oct. 30, 2006.

Perera, R.W.H., et al., "Assessment of chiral stationary phases for suitability for combined enantiomeric impurity/related substances assays," Journal of Chromatography A, 1218 (2011) 8655-8663.

* cited by examiner

COMPOSITION FOR TREATING ATOPY OR PRURITUS COMPRISING N-ACETYL OR N-ACYL AMINO ACID

CROSS-REFERENCE TO RELATED APPLICATIONS

This application is a divisional application of U.S. patent application Ser. No. 16/766,891, filed on May 26, 2020, which is a § 371 national stage entry of International Application No. PCT/KR2018/014483, filed on Nov. 23, 2018, which claims priority to Korean Patent Application No. 10-2018-0145159, filed on Nov. 22, 2018, and Korean Patent Application No. 10-2017-0158599, filed on Nov. 24, 2017, the entire contents of which are incorporated herein by reference.

TECHNICAL FIELD

The present disclosure relates to a composition for preventing or treating atopy, pruritus or atopy accompanied by pruritus, moisturizing skin or soothing skin, which contains an N-acetyl or N-acylamino acid as an active ingredient.

BACKGROUND ART

Pruritus (itch) is defined as an unpleasant sensation that causes the desire to scratch or rub skin (Andersen H H et al., Human surrogate models of histaminergic and non-histaminergic itch, *Acta Dermato-Venereologica*. 95 (7): 7717. (2015)). Although it is a symptom commonly observed in skin diseases and systemic diseases, its characteristics are not fully known yet.

It is known that about 280 million people globally, 4% of the world population, have difficulty with pruritus, with higher incidence than psoriasis (2-3%) (Vos, T et al., Years lived with disability (YLDs) for 1160 sequelae of 289 diseases and injuries 1990-2010: a systematic analysis for the Global Burden of Disease Study 2010, *Lancet*. 380 (9859): 216396. (2012)).

Pruritus can be induced or aggravated by various stimuli including physical, mechanical and chemical factors. In addition, inflammation-mediating substances induce pruritus in various inflammatory skin diseases. However, not all types of pruritus are associated with the mediating substances, and pruritus caused by mechanical stimulation, electrical stimulation or skin dryness may occur regardless of mediating substances.

According to the data of the Korean National Health Information Portal (http://health.mw.go.kr), histamine, serotonin, prostaglandin E, tachykinin, cytokines, proteases, opioid peptides, platelet-activating factor, etc. are known as pruritus-inducing mediating substances.

For treatment of pruritus, various therapies are available for now, such as antihistamines, steroids, antibiotics, antiviral drugs, antifungal medicines, anesthetics, probiotics, immunosuppressants, phototherapy such as UV, etc., but the therapeutic effect is temporary or limited depending on the type of pruritus. In addition, adrenocorticotropic hormones and corticosteroids can be used only in short term for acute or severe cases due to side effects.

Atopic dermatitis is an eczema-like skin lesion occurring in people with atopic constitution. It is also called endogenous eczema or Besnier's purigo. The cause is unknown but believed to involve genetics. It shows distinct symptoms and progress distinguished from other common eczema or dermatitis. 70-80% of infantile eczema is due to atopic dermatitis. The symptoms vary with age and are usually classified into three stages. (1) Infancy (around 2 months to 3 years): Flare, exudation and desquamation occur on the face, particularly on the cheeks, and the itch is very severe. If the symptoms are aggravated, the same change occurs also on the scalp together with scurf and flare and desquamation occur on the skin throughout the body. The whole skin turns rough and bluish white. The symptoms occur around 2-3 months after birth and heal well by one year of age, but can recur. In general, the symptoms are aggravated in winter. (2) Childhood (around 4-10 years): Papules and purigo around 4-5 years on the limbs (particularly on the front elbow and the back of the knee) and develop into lichenification. (3) Adolescence (12 years and older): Lichenification occurs not only on the limbs but also on the face, chest, nape, etc. Pediatric asthma often occurs together, and family members tend to develop asthma or atopic dermatitis. Because the symptoms last long and do not heal well, long-term patient treatment is necessary. However, the symptoms are ameliorated with age. For severe symptoms, ointments (antihistamine, vitamin A or vitamin D) are used and antipruritics are used together (Doosan Encyclopedia, http://www.doopedia.co.kr/).

The cause of pruritus and atopic dermatitis is unclear in many cases and, despite the presence of various therapeutic agents including steroids, the therapeutic effect is only temporary or limited. In addition, the steroid drugs have side effect problems associated with misuse or abuse.

Therefore, development of a new safe therapy which is effective for pruritus and/or atopic dermatitis caused by various causes is keenly needed.

The foregoing description of the background art is intended only to help understanding of the background of the present disclosure and it should not be construed as accepting that the background art is already well known to those of ordinary skill in the art.

DISCLOSURE

Technical Problem

The inventors of the present disclosure have made efforts to find a substance that can be safely prescribed for pruritus and/or atopic dermatitis caused by various causes with no concern about side effects. As a result, they have identified that an N-acetyl or N-acylamino acid is very effective for pruritus and/or atopy and have completed the present disclosure.

Accordingly, the present disclosure is directed to providing a composition for preventing, improving or treating atopy.

The present disclosure is also directed to providing a composition for preventing, improving or treating pruritus.

The present disclosure is also directed to providing a composition for preventing, improving or treating atopy and pruritus.

The present disclosure is also directed to providing a composition for moisturizing skin or soothing skin.

Other objects and advantages of the present disclosure will be more clearly understood from the following detailed description, claims and drawings.

Technical Solution

In an aspect of the present disclosure, the present disclosure provides a composition for preventing, improving or treating atopy, which contains an N-acetylamino acid, an N-acylamino acid or a salt thereof as an active ingredient.

In another aspect of the present disclosure, the present disclosure provides a composition for preventing, improving or treating pruritus, which contains an N-acetylamino acid, an N-acylamino acid or a salt thereof as an active ingredient.

In another aspect of the present disclosure, the present disclosure provides a composition for preventing, improving or treating atopy and pruritus, which contains an N-acetylamino acid, an N-acylamino acid or a salt thereof as an active ingredient.

The inventors of the present disclosure have made efforts to find a substance that can be safely prescribed for pruritus and/or atopic dermatitis caused by various causes with no concern about side effects. As a result, they have identified that an N-acetyl or N-acylamino acid is very effective for pruritus and/or atopy.

In the present disclosure, the term activity of preventing, improving or treating "atopy" refers to the activity of preventing, improving or treating atopic disease or atopic syndrome. The atopic disease or atopic syndrome collectively refers to a disease or syndrome caused by allergic reactions whereby the human body becomes extremely sensitive upon contact or without direct contact with an allergic antigen. Examples include atopic allergy, atopic eczema, atopic dermatitis, allergic conjunctivitis, allergic rhinitis, asthma, etc., although not being limited thereto.

According to examples of the present disclosure, the composition of the present disclosure shows therapeutic effect for atopic dermatitis in an in-vivo experiment on an animal model of Balb/c mouse in which atopic dermatitis is induced with 2,4-dinitrofluorobenzene (DNFB) (Example 4), significantly decreases the level of immunoglobulin E (IgE) increased in atopic dermatitis (Example 5), and significantly decreases the expression of interleukin-4 (IL-4) and interferon γ, which are TH2 immunoregulatory cytokines associated with the lesion of atopic dermatitis (Example 6).

In the present disclosure, the term "pruritus" or "itch" is not specially limited and is understood to include paroxysmal pruritus, winter pruritus, anal pruritus, vulvar pruritus, scrotal pruritus, aquagenic pruritus, scalp pruritus, nasal pruritus, neck itch, oral pruritus, ocular pruritus, cholestatic pruritus, pruritus accompanied by internal diseases such as chronic renal failure, malignant tumor, iron-deficiency anemia, polycythemia vera, hyperthyroidism, hypothyroidism, diabetes, acquired immune deficiency syndrome, etc. and pruritus accompanied by systemic skin diseases such as lichen simplex chronicus, prurigo, trichotillomania, neurotic excoriation, skin-picking behavioral disorder, delusional parasitosis, etc.

Paroxysmal pruritus is paroxysmally occurring pruritus and is found in lichen simplex chronicus, dermatitis, etc.

Winter pruritus occurs in about 50% or more of people aged 70 years or older and should be distinguished from pruritus caused by pruritic skin diseases or systemic diseases such as scabies, lichen planus, etc. For women, it may occur as a symptom of postmenstrual syndrome. Skin dryness due to decreased water content and gradually decreased sebum secretion in aged skin is the major cause and fine fissures and scaling occur mainly in the upper limbs and tibial regions.

Anal pruritus is the unpleasant sensation around the anus, causing the desire to scratch, and is frequently associated with psychogenic factors. It may occur regardless of age but occurs more frequently after middle life. However, not all the causes of anal pruritus are psychogenic, and contamination and irritation around the anus may be the cause. The irritation may be aggravated by colorectal and anal diseases such as anal fissure, hemorrhoids, anal fistula and chronic diarrhea, pungent food, medications, etc. Various infectious diseases by *Staphylococcus, Streptococcus*, molds, Candida, herpes simplex virus, etc. may induce pruritus. Among them, Candida infection is the commonest and causes fissures and sodden epidermis. Skin diseases around the anus, such as soriasis, seborrhoeic dermatitis, lichen planus, etc., may also cause severe pruritus and lesions can be observed in other parts, too. Anal neurodermatitis is characterized by violent itching, at which time the patient may tear at the affected area until bleeding is induced. Manifestations may be identical to lichen simplex chronicus elsewhere on the body.

Candida infection is the most frequent cause of vulvar pruritus. Other causes may include trichomonas vaginitis or contact dermatitis caused by pads, contraceptive devices, vaginal wash, condoms, etc. After middle life, lichen sclerosus et atrophicus is the commonest cause. Severe pruritus may occur also in Fox-Fordyce disease. However, temporary vulvar pruritus may also be caused by abrasion, sweating, vulvar congestion during pregnancy, etc.

Regarding scrotal pruritus, the scrota of adults are immune to fungal infection like the scalp but lichen simplex chronicus occurs frequently there. The cause may be psychogenic in many cases. Severe lichenification may occur and the symptoms can last a few years despite intensive treatment.

Aquagenic pruritus is characterized by the development of severe, unpleasant, pricking-like itching evoked by contact with water occurring within several minutes after the contact or even after the contact has been discontinued. It is irrelevant to the temperature of water and no special change is observed on the skin. In some patients, it can occur due to the change in ambient temperature. About ⅓ of patients show family history. It is usually chronic and does not respond well to treatment. Although increased histamine level is observed on skin and in blood, the symptoms are not ameliorated by antihistamines. Hence, it is thought that histamine is not the only cause. Distinction is necessary because the symptoms are similar to those of polycythemia vera.

Scalp pruritus can occur independently without distinct lesions on the scalp. It occurs in middle-aged and elderly people, but the cause is not known well. The itchiness is very severe, occurs paroxysmally, and is aggravated by fatigue or stress. It needs to be distinguished from herpetic dermatitis, lichen simplex chronicus, seborrhoic dermatitis, psoriasis, etc.

Patients with biliary hepatocirrhosis suffer from severe systemic pruritus. The pruritus is associated with increased level of bile acid in blood plasma. Application of bile acid at a concentration clinically inducing pruritus directly onto blistery skin lesions may induce severe pruritus.

Pruritus occurs in about 20-50% of chronic renal failure patients receiving hemodialysis treatment. The pruritus occurs topically or systemically. The symptoms become severe mostly during hemodialysis, but the hemodialysis may temporarily alleviate the symptoms. It is reported that there is no direct relationship between the concentration of histamine, urea and creatinine in blood and the severity of pruritus. Although some patients show skin dryness, most have normal skin and the use of moisturizers does not alleviate or relieve the symptom.

If systemic pruritus occurs in middle or old ages without special reason, extensive examination of malignant tumor is necessary. Pruritus occurs consistently in 15-25% of patients with Hodgkin's disease (a representative example of lymphoma). Sometimes burning pain and flushing sensation are accompanied, although the cause is not known. Systemic pruritus can occur also in leukemia.

Iron deficiency may also be the cause of pruritus. It is reported that oral administration of iron supplements to patients with polycythemia vera and iron deficiency decreased pruritus.

About 50% of patients with polycythemia vera experience severe pruritus within several minutes after exposure to water, which lasts for about 15-60 minutes. It is called bath itch since it usually occurs after taking a bath. No special change is observed on the skin and it occurs irrespective of the water temperature. But, increased histamine level is observed in serum and urine. It is though that platelet aggregation is the cause inducing several pruritus-mediating substances including histamine.

Severe systemic pruritus can occur in hyperthyroidism. Increased cutaneous blood flow increases the skin surface temperature and lowers the itch threshold. In hypothyroidism, systemic pruritus may occur due to severe skin dryness caused by myxoedema. In both diseases, pruritus may occur around the genital areas due to mucocutaneous candidiasis.

In some diabetic patients, pruritus may occur around the genital areas due to mucocutaneous candidiasis. However, systemic pruritus may occur in other patients.

Pruritus is one of the major symptoms of acquired immune deficiency syndrome. The cause of pruritus in patients with acquired immune deficiency syndrome includes scabies, pediculosis, candidiasis, seborrhoic dermatitis and systemic diseases such as renal failure, cholestasis, etc. In addition, systemic papule or pigmented rash causing characteristically severe pruritus often occurs.

Lichen simplex chronicus is a disease characterized by repeated rubbing or scratching of the skin, causing thick, leathery skin. Lichen simplex chronicus may occur secondarily in normal skin as a result of repeated pruritus. In general, it is more common in 30 s to 50 s and is seen more often in women compared to men.

Prurigo is a disease characterized by multiple nodules and severe pruritus. It is not cured well and tends to last for a long time. Its cause is not known well and anemia, liver disease, HIV, pregnancy, renal failure, mental stress, etc. may be the cause.

Trichotillomania is a mental disorder characterized by an abnormal urge that results in the pulling out of one's hair. Mental and social stresses are the cause. Stress in family or school lives, sibling rivalry, move, hospitalization of parents, mother-daughter relationship, etc. may be the cause. It occurs in nearly all age groups from children to adults.

Neurotic excoriation is a disease characterized by the repeated and compulsive urge to pick and gouge one's own skin, often leading to skin lesions. Patients admit that their behavior is responsible for the lesions but cannot resist it. It can occur at any age but occurs more frequently in middle-aged women. It often occurs due to mental stress. It often occurs on skin lesion areas such as pruritus, insect sting, etc. Neurotic excoriation also correlates with depression, obsessive-compulsive disorder and anxiety. This symptom occurs more frequently in people with obsessive, stubborn, supervisory characteristics and perfectionism tendencies with fear for failure.

Factitious dermatitis is a dermatitis occurring from intentional self-inflicted skin damage in an attempt to attract sympathy or avoid responsibility. Skin lesions are produced mechanically or by chemicals, corrosives, etc. In addition, nails, sharp instruments, hot metals, etc. are used too. The patient harms himself/herself in order to satisfy psychological needs. It occurs more frequently in women and can occur in all age groups. Most patients are childish and dependent and have impulse control disorders.

Skin-picking behavioral disorder is an obsessive self-inflicting behavior repeated for a long time. The self-inflicting behavior often leads to a suicidal attempt and, in adolescence, it may be attempted to show off bravery.

Delusional parasitosis is a delusional disorder in which patients incorrectly believe they are infested with parasites. It is a chronic, monosymptomatic hypochondriasis without damage to personality or thinking ability. Patients provide pieces of skin, lint, tissue paper, tape, etc. and ask for parasite examination. It is reported that 2-3% of the patients have experienced parasitic infection before.

In addition, there are nasal pruritus accompanied by nasal diseases such as rhinitis, ocular pruritus accompanied by ocular diseases such as conjunctivitis, and oral pruritus accompanied by dental diseases.

According to an example of the present disclosure, the composition of the present disclosure showed a remarkable effect of suppressing pruritus in an in-vivo experiment on an animal model of Balb/c mouse in which pruritus is induced with 2,4-dinitrofluorobenzene (DNFB) (Example 8).

In a specific exemplary embodiment of the present disclosure, the composition of the present disclosure is used for preventing, improving or treating atopy accompanied by pruritus.

TSLP (thymic stromal lymphopoietin) is known to play an important role in the maturation of T cells through activation of antigen-presenting cells, and is also known to cause TH2 inflammatory responses by inducing CD11c+ myeloid dendritic cells (Ziegler S F et al., Thymic stromal lymphopoietin in normal and pathogenic T cell development and function. *Nat Immuno/*2006; 7: 709-14). It is known that the TSLP is increased in the lesions of atopy patients and is associated with the severity of atopic dermatitis (Sano Y et al., Thymic stromal lymphopoietin expression is increased in the horny layer of patients with atopic dermatitis. *Clin Exp Immunol* 2013; 171: 330-7).

Unlike other inflammatory diseases, atopic dermatitis is characterized in that it is accompanied by pruritus. It was identified that, in addition to the correlation to the severity of atopic dermatitis, the TSLP is the cause of pruritus in atopic dermatitis (Wilson S R et al., The epithelial cell-derived atopic dermatitis cytokine TSLP activates neurons to induce itch. *Cell.* 2013; 155 (2): 285-95).

Accordingly, the composition of the present disclosure may be effectively used in prevention, improvement or treatment of atopy accompanied by pruritus.

In a specific exemplary embodiment of the present disclosure, the N-acetylamino acid is one or more amino acid selected from a group consisting of N-acetylalanine, N-acetylthreonine, N-acetylarginine and N-acetyltryptophan.

In a specific exemplary embodiment of the present disclosure, the N-acetylamino acid is one or more amino acid selected from a group consisting of N-acetyl-L-alanine, N-acetyl-L-threonine, N-acetyl-L-arginine and N-acetyl-L-tryptophan.

In a specific exemplary embodiment of the present disclosure, the N-acylamino acid is N-acyltryptophan or N-acylalanine.

In a specific exemplary embodiment of the present disclosure, the N-acylamino acid is N-acyl-L-tryptophan or N-acyl-L-alanine.

In the present disclosure, the term "acyl" or "acyl group" refers to a radical having the general formula RCO, derived by the removal of a hydroxyl (OH) group from a carboxylic acid, without special limitation. R may be one or more of any substituent that can be bonded to CO, without limitation. Particularly, if R is an aromatic radical, the group is called "aroyl", which is also an acyl group. Examples of the acyl group include formyl (HCO—), acetyl (CH$_3$CO—), propionyl (C$_2$H$_5$CO—), butyryl (C$_3$H$_7$CO—), valeryl (C$_4$H$_9$CO—), pentanoyl (CH$_3$(CH$_2$)$_3$CO—), palmitoyl (C$_{15}$H$_{31}$CO—), stearoyl (C$_{17}$H$_{33}$CO—), oleoyl (C$_{17}$H$_{31}$CO—), oxalyl (—CO—CO—), malonyl (—COCH$_2$CO—), succinyl (—CO(CH$_2$)2CO—), benzoyl (C$_6$H$_5$CO—), toluoyl (CH$_3$—C$_6$H$_4$—CO—), salicyloyl (HO—C$_6$H$_4$—CO—), cinnamoyl (C$_6$H$_5$CH=CHCO—), naphthoyl (C$_{10}$H$_7$CO—), phthaloyl (CO—C$_6$H$_4$—CO—), furoyl

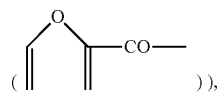

undecanoyl (CH$_3$(CH$_2$)$_9$CO—) and docosenoyl with an OH group removed from docosenoic acid, although not being limited thereto.

Specifically, the N-acyl-L-tryptophan is one or more amino acid selected from a group consisting of N-propionyl-L-tryptophan, N-butyryl-L-tryptophan, N-pentanoyl-L-tryptophan, N-undecanoyl-L-tryptophan, N-palmitoyl-L-tryptophan, N—(Z)-docos-13-enoyl-L-tryptophan, N-stearyl-L-tryptophan and N-oleoyl-L-tryptophan, although not being limited thereto.

Specifically, the N-acyl-L-alanine is N-acetyl-γ-glutammyl-L-alanine or N-palmitoyl-L-alanine, although not being limited thereto.

In the present disclosure, the term "containing as an active ingredient" refers to an amount sufficient to achieve the effect or activity of the N-acetyl or N-acylamino acid. In a specific exemplary embodiment of the present disclosure, the N-acetyl or N-acylamino acid is contained in the composition of the present disclosure in an amount of, for example, 0.001 mg/kg or more, specifically 0.1 mg/kg or more, more specifically 1 mg/kg or more, further more specifically 10 mg/kg or more. Because the N-acetyl or N-acylamino acid has few side effects on the human body even when administered in excess amounts, the upper limit of the amount of the N-acetyl or N-acylamino acid contained in the composition of the present disclosure may be adequately determined by those skilled in the art.

It is understood that the N-acetyl or N-acylamino acid, which is contained in the composition of the present disclosure as an active ingredient, includes, not only the compound itself, but also its pharmaceutically, sitologically or cosmetically acceptable salt, hydrate, solvate or prodrug.

In the present disclosure, the term "pharmaceutically acceptable salt", "sitologically acceptable salt" or "cosmetically acceptable salt" refers to salt of the compound which does not negatively affect the biological activity and physical properties of the compound and does not induce severe stimulation in an organism to which the compound is administered. The pharmaceutically, sitologically or cosmetically acceptable salt may be obtained by reacting the compound of the present disclosure with an inorganic acid such as, hydrochloric acid, bromic acid, sulfuric acid, nitric acid, phosphoric acid, etc., a sulfonic acid such as methanesulfonic acid, ethanesulfonic acid, p-toluenesulfonic acid, etc., or an organic acid such as tartaric acid, formic acid, citric acid, acetic acid, trichloroacetic acid, trifluoroacetic acid, capric acid, isobutanoic acid, malonic acid, succinic acid, phthalic acid, gluconic acid, benzoic acid, lactic acid, fumaric acid, maleic acid, salicylic acid, etc. In addition, the salt may be obtained by reacting the compound of the present disclosure with a base to form an ammonium salt, an alkali metal salt such as a sodium or potassium salt, etc., an alkaline earth metal salt such as a calcium or magnesium salt, a slat with an organic base such as dicyclohexylamine, N-methyl-D-glucamine, tris(hydroxymethyl)methylamine, etc., or an amino acid salt with arginine, lysine, etc., although not being limited thereto.

The term, "pharmaceutically acceptable hydrate", "sitologically acceptable hydrate" or "cosmetically acceptable hydrate" refers to a hydrate of the N-acetyl or N-acylamino acid which exert the desired pharmacological effect. The term "pharmaceutically acceptable solvate", "sitologically acceptable solvate" or "cosmetically acceptable solvate" refers to a solvate of the N-acetyl or N-acylamino acid compound which exert the desired pharmacological effect. The hydrate and the solvate may also be prepared by using the above-descried acids, and they are also included in the pharmaceutically, sitologically or cosmetically acceptable salt in a broad sense.

The term "pharmaceutically acceptable prodrug", "sitologically acceptable prodrug" or "cosmetically acceptable prodrug" refers to a derivative of the N-acetyl or N-acylamino acid which has to undergo bioconversion prior to exhibiting the pharmacological effect of the N-acetyl or N-acylamino acid. The prodrug is prepared to improve chemical stability, patient compliance, bioavailability or organ selectivity, to improve convenience of preparation, to prolong the duration of action, or to reduce side effects. The prodrug of the present disclosure may be prepared easily using the N-acetyl or N-acylamino acid according to a method commonly employed in the art (e.g., Burger's Medicinal Chemistry and Drug Chemistry, 5th ed., 1: 172-178 and 949-982 (1995)).

In a specific exemplary embodiment of the present disclosure, the composition of the present disclosure is a pharmaceutical composition.

A pharmaceutically acceptable carrier contained in the pharmaceutical composition of the present disclosure may be one commonly used in the art and may include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain, in addition to these ingredients, a lubricant, a wetting agent, a sweetener, a flavor, an emulsifier, a suspending agent, a preservative, etc. Suitable pharmaceutically acceptable carriers and formulations are described in detail in Remington's Pharmaceutical Sciences (19th ed., 1995).

The pharmaceutical composition of the present disclosure may be administered orally or parenterally. The parenteral administration can be made nasally, ocularly, intravenously, subcutaneously, intramuscularly, intraperitoneally, transdermally, etc.

An adequate administration dosage of the pharmaceutical composition of the present disclosure may vary depending on such factors as formulation method, administration method, the age, body weight and sex of a patient, pathological condition, diet, administration time, administration route, excretion rate and responsiveness. An ordinarily skilled physician can easily determine and prescribe an administration dosage which is effective for the desired treatment or prevention. In a specific exemplary embodiment of the present disclosure, a daily administration dosage of the pharmaceutical composition of the present disclosure is 0.001-100 mg/kg.

The pharmaceutical composition of the present disclosure may be formulated as a unit dosage form or in a multiple-dosage receptacle by using a pharmaceutically acceptable carrier and/or excipient according to a method that can be easily carried out by those of ordinary skill in the art to which the present disclosure belongs. The formulation may be in the form of a solution in an oily or aqueous medium, a suspension, an emulsion, an extract, a powder, a granule, a tablet or a capsule and may further contain a dispersant or a stabilizer.

The pharmaceutical composition of the present disclosure may also be prepared into a formulation for external application to skin, an aerosol, a spray, an eye drop, an oral medication or an injection.

The pharmaceutical composition of the present disclosure may be used for human or animals.

In a specific exemplary embodiment of the present disclosure, the composition of the present disclosure is a food composition.

The food composition according to the present disclosure may be used as a functional food or may be added to various foods. The foods to which the composition of the present disclosure can be added include, for example, beverages, alcohol beverages, confectionery, diet bar, dairy products, meat, chocolate, pizza, bakery, ramen, other noodles, gums, ice creams, multivitamin supplements, health food supplements, etc.

The food composition of the present disclosure may contain, in addition to the N-acetyl or N-acylamino acid as the active ingredient, an ingredient commonly added during preparation of food, for example, a protein, a carbohydrate, a fat, a nutrient, a seasoning agent or a flavoring agent. Examples of the carbohydrate are common sugars such as monosaccharides, e.g., glucose, fructose, etc., disaccharides, e.g., maltose, sucrose, oligosaccharides, etc., and polysaccharides, e.g., dextrin, cyclodextrin, etc.; and sugar alcohols such as xylitol, sorbitol, erythritol, etc. As the flavoring agent, a natural flavor (thaumatin or stevia extract (e.g., rebaudioside A, glycyrrhizin, etc.)) or a synthetic flavor (saccharin, aspartame, etc.) may be used. For example, when the food composition of the present disclosure is prepared as a drink or a beverage, it may further contain, in addition to the N-acetyl or N-acylamino acid, citric acid, fructose syrup, sucrose, glucose, acetic acid, malic acid, fruit juice, various plant extracts, etc.

The present disclosure provides a functional health food as a food composition containing an N-acetyl or N-acylamino acid or a sitologically acceptable salt as an active ingredient. The functional health food refers to a food prepared by adding the N-acetyl or N-acylamino acid to a foodstuff such as a drink, a tea, a spice, a gum, confectionery, etc. or preparing into a capsule, a powder, a suspension, etc. to provide special health effect. Unlike general medicines, it is advantageous in that there is no side effect that may occur during long-term use of medicines. The functional health food of the present disclosure is very useful because it can be ingested routinely. The content of the N-acetyl or N-acylamino acid in functional health food may vary depending on the type of the functional health food within a range not negatively affecting the inherent taste of the food. Usually, its content in the food is 0.01-50 wt %, specifically 0.1-20 wt %. And, when the functional health food is in the form of a pill, a granule, a tablet or a capsule, it may be added in an amount of usually 0.1-100 wt %, specifically 0.5-80 wt %. In a specific exemplary embodiment, the functional health food of the present disclosure may be in the form of a pill, a tablet, a capsule or a drink.

The food composition of the present disclosure may be used as a food for human, a feed for animals, a feed additive, etc.

In a specific exemplary embodiment of the present disclosure, the composition of the present disclosure is a cosmetic composition.

In another aspect of the present disclosure, the present disclosure provides a cosmetic composition for moisturizing skin or soothing skin, which contains an N-acetylamino acid, an N-acylamino acid or a cosmetically acceptable salt as an active ingredient.

In a specific exemplary embodiment of the present disclosure, the cosmetic composition of the present disclosure improves one or more skin condition selected from a group consisting of skin dryness, edema, erythema, inflammation, eschar, abrasion and lichenification.

When the composition of the present disclosure is prepared as a cosmetic composition, the composition of the present disclosure may further contain, in addition to the N-acetyl or N-acylamino acid, an ingredient commonly used in a cosmetic composition, for example, a commonly used adjuvant such as an antioxidant, a stabilizer, a solubilizer, a vitamin, a pigment and a flavor, and a carrier. Besides, the composition of the present disclosure may further contain, in addition to the N-acetyl or N-acylamino acid, an atopy-improving agent, a pruritus-improving agent, or an agent for moisturizing or soothing skin which has been used hitherto within a range not negatively affecting the (atopy and/or pruritus-improving) action of the active ingredient.

As the carrier, purified water, a monohydric alcohol (ethanol or propyl alcohol), a polyhydric alcohol (glycerol, 1,3-butylene glycol or propylene glycol), a higher fatty acid (palmitic acid or linoleic acid), an oil or fat (wheat germ oil, camellia oil, jojoba oil, olive oil, squalene, sunflower oil, macadamia nut oil, avocado oil, hydrogenated soybean lecithin or fatty acid glyceride), etc. may be used, although not being limited thereto. If necessary, a surfactant, a sterilizer, an antioxidant, a UV absorber, an anti-inflammatory agent or a cooling agent may be further added.

The surfactant may be selected from a group consisting of polyoxyethylene, hydrogenated castor oil, polyoxyethylene oleyl ether, polyoxyethylene monooleate, polyoxyethylene glyceryl monostearate, sorbitan monostearate, sorbitan, sucrose fatty acid ester, hexaglyceryl monolaurate, polyoxyethylene-reduced lanolin, POE, glyceryl pyroglutamate, isostearic acid diester, N-acetylglutamine and isostearyl ester.

The sterilizer may be selected from a group consisting of hinokitiol, triclosan, chlorhexidine gluconate, phenoxyethanol, resorcin, isopropylmethylphenol, azulene, salicylic acid and zinc pyrithione.

As the antioxidant, any of butylhydroxyanisole, gallic acid, propyl gallate and erythorbic acid may be used.

As the UV absorber, any of a benzophenone such as dihydroxybenzophenone, etc., melanin, ethyl p-aminobenzoate, p-dimethylaminobenzoic acid 2-ethylhexyl ester, cinoxate, p-methoxycinnamic acid 2-ethylhexyl ester, 2-(2-hydroxy-5-methylphenyl)benzotriazole, urocanic acid and fine metal oxide particle may be used.

As the anti-inflammatory agent, dipotassium glycyrrhetinate or allantoin may be used. And, as the cooling agent, capsicum tincture or 1-menthol may be used.

The composition may be prepared into any formulation in which the N-acetyl or N-acylamino acid can be mixed as an active ingredient. Examples of the cosmetic formulation for improving atopy or pruritus include a tonic, a shampoo, a rinse, a hair conditioner, a hair spray, a powder, a gel, a cream, an essence, a lotion, a sol-gel, an emulsion, an oil, a wax, a spray, a mist, etc., although not being limited thereto. In addition, it may be prepared as a mask pack containing the N-acetyl or N-acylamino acid.

Advantageous Effects

The features and advantages of the present disclosure may be summarized as follows:

(i) The present disclosure provides a composition for preventing, improving or treating atopy by using an N-acetyl or N-acylamino acid, which has few side effects on the human body.

(ii) In addition, the present disclosure provides a composition for preventing, improving or treating pruritus by using an N-acetyl or N-acylamino acid.

(iii) The composition of the present disclosure may be usefully used to improve or treat pruritus and/or atopic dermatitis caused by various causes safely and effectively without the concern of side effects.

BEST MODE FOR CARRYING OUT INVENTION

Hereinafter, the present disclosure will be described in detail through examples. However, the following examples are for illustrative purposes only and it will be obvious to those of ordinary skill in the art that the scope of the present disclosure is not limited by the examples.

EXAMPLES

<Example 1> Test Animals and Reagents 7-week-old male Balb/c mice and 7-week-old male Nc/Nga mice were purchased from Orient Bio (Seongnam, Gyeonggi-do, Korea) and maintained under specific pathogen-free conditions. The mice were housed in an air-conditioned animal room at a temperature of 25±1° C. and a relative humidity of 40±5%, and they were given distilled water and laboratory diet. Animal treatment and maintenance complied with the Principles of Laboratory Animal Care (NIH Publication No. 85-23, revised in 1985) and the guidelines of the Institutional Animal Care and Use Committee of the Jeonbuk National University (KHUASP (SE)-15-021). All procedures were conducted in accordance with the guidelines of the United States National Institute of Health (NIH).

<Example 2> Induction of Atopic Dermatitis

Figure 1A:
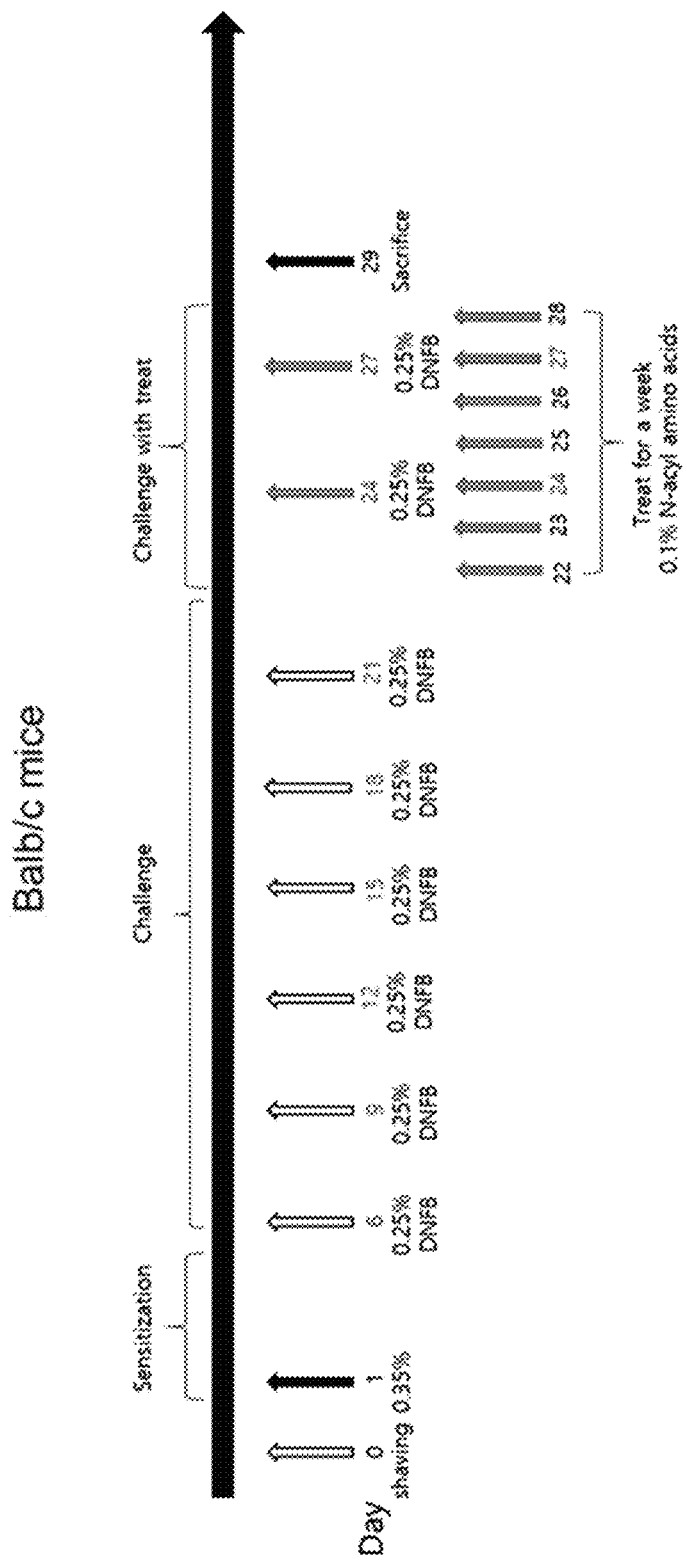
FIG. 1A shows a process of inducing atopic dermatitis-like skin lesions by repeatedly applying 2,4-dinitrofluorobenzene (DNFB) to Balb/c mouse and administering a drug.

In order to induce atopy-like dermatitis in Balb/c mice, DNFB sensitization was induced by applying 100 μL of 0.35% 2,4-dinitrofluorobenzene (DNFB) (Sigma, USA) in acetone/olive oil (3:1) on the shaved back skin of the mice. Then, dermatitis was induced by applying 100 μL of 0.25% DNFB on days 6, 9, 12, 15, 18 21, 24 and 27 on the shaved back skin. Control mice were treated with a vehicle of the same volume (FIG. 1A).

Figure 1B:
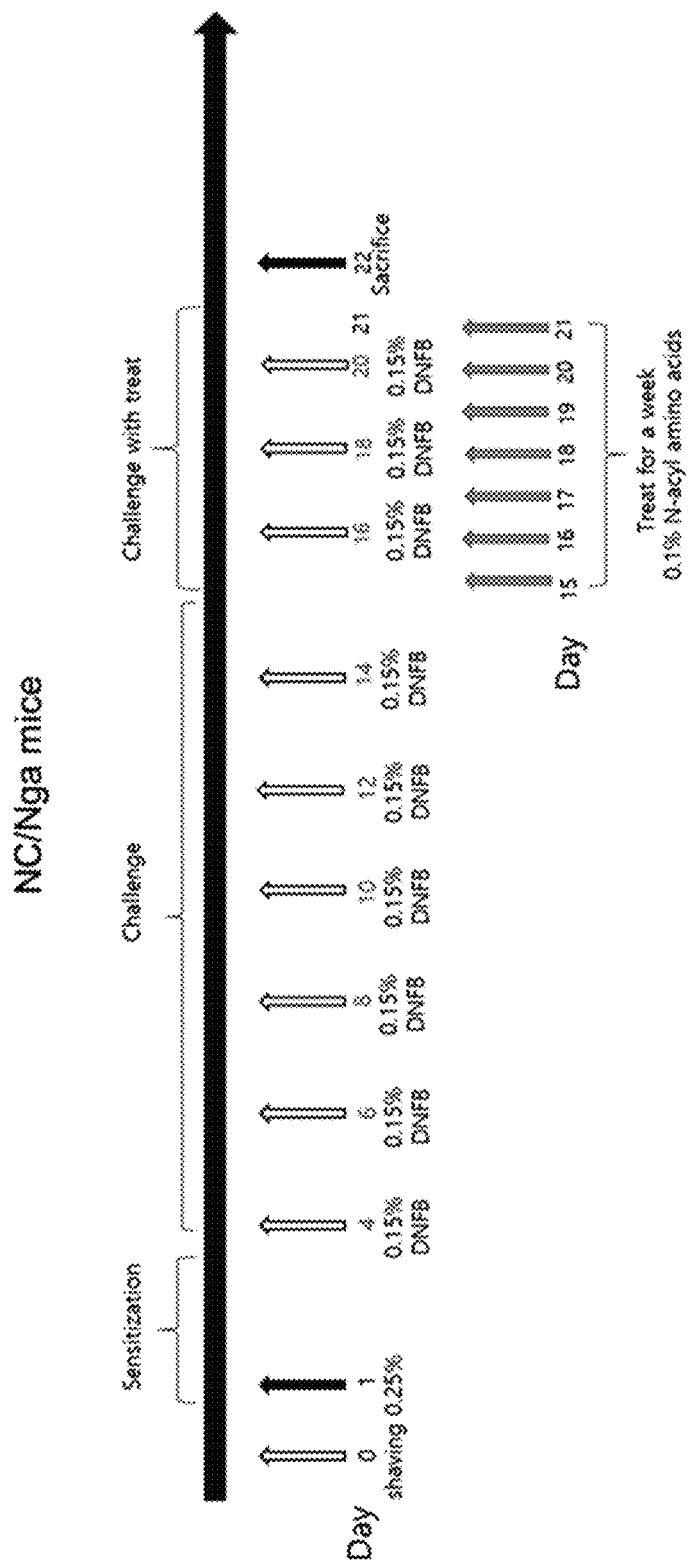
FIG. 1B shows a process of inducing atopic dermatitis lesions by repeatedly applying 2,4-dinitrofluorobenzene (DNFB) to Nc/Nga mouse and administering a drug.

In order to establish a model more similar to an atopy model than that of the Balb/c mice, atopy was induced in Nc/Nga mouse mice. Specifically, after inducing DNFB sensitization by applying 100 μL of 0.35% 2,4-dinitrofluorobenzene (DNFB) in acetone/olive oil (3:1) on the shaved back skin, dermatitis was induced by applying 100 μL of 0.15% DNFB for 4-20 days, every other day. Control mice were treated with a vehicle of the same volume (FIG. 1B).

<Example 3> Drug Treatment

After dissolving an N-acetyl or N-acylamino acid in phosphate-buffered saline to 0.1%, 200 μL of the solution was applied on the back skin of the mice every day, from day 22 until day 28 for the Balb/c atopic dermatitis model, and from day 15 until day 21 for the Nc/Nga atopic dermatitis model. When the N-acetyl or N-acylamino acid was treated together with DNFB, they were treated with 12-hour intervals in order to avoid direct reaction between the DNFB and the N-acetyl or N-acylamino acid. A non-treated group and a 2,4-dinitrofluorobenzene (DNFB) group were treated with phosphate-buffered saline of the same volume (FIGS. 1A-1B). As the N-acetylamino acid, products purchased from Sigma-Aldrich (USA), MP scientific (USA), TCI (Tokyo Chemical Industry, Japan), Santacruz (USA), etc. were used without purification.

<Example 4> Evaluation of Skin-Soothing Effect and Severity of Atopic Dermatitis The degree of skin soothing and the severity of atopic dermatitis were evaluated macroscopically according to the previously established SCORAD (SCORing Atopic Dermatitis) method (Oranje et al., 2007). The degree of symptoms such as edema, erythema, eschar, dryness, abrasion, lichenification, etc. was graded from 0 to 3 (0, no symptom; 1, mild; 2, moderate; 3, severe). The overall dermatitis score was determined from the sum of all individual scores (Table 1). The assessment was performed by an investigator who was blind to the grouping of the mice. As seen from Table 1, from among the 20 N-acetyl-L-amino acids, N-acetyl-L-cysteine, N-acetyl-L-alanine, N-acetyl-L-arginine, N-acetyl-L-threonine and N-acetyl-L-tryptophan showed significant skin-soothing and atopic dermatitis-treating effects.

TABLE 1

|  | Mouse 1 | | | | | | | Mouse 2 | | | | |
| --- | --- | --- | --- | --- | --- | --- | --- | --- | --- | --- | --- | --- |
|  | Erythema | Edema | Eschar | Dryness | Abrasion | Lichenification | Sum | Erythema | Edema | Eschar | Dryness | Abrasion |
| Control | 0 | 0 | 0 | 0 | 0 | 0 | 0 | 0 | 0 | 0 | 0 | 0 |
| DNFB (D) | 3 | 2 | 2 | 3 | 2 | 3 | 15 | 2 | 3 | 2 | 2 | 3 |
| D + N-acetyl-L-cysteine | 2 | 2 | 2 | 2 | 2 | 3 | 13 | 2 | 1 | 2 | 3 | 2 |
| D + N-acetyl-L-alanine | 1 | 1 | 1 | 2 | 1 | 0 | 6 | 1 | 1 | 1 | 0 | 1 |
| D + N-acetyl-L-asparagine | 3 | 2 | 2 | 3 | 3 | 2 | 152 | 2 | 2 | 3 | 2 | 3 |
| D + N-acetyl-L-phenylalanme | 3 | 2 | 1 | 3 | 2 | 2 | 13 | 3 | 2 | 2 | 3 | 2 |
| D + N-acetyl-L-aspartic acid | 3 | 2 | 2 | 2 | 2 | 2 | 13 | 3 | 2 | 2 | 3 | 2 |
| D + N-acetyl-L-threonine | 1 | 1 | 1 | 2 | 1 | 1 | 7 | 1 | 1 | 1 | 0 | 1 |
| D + N-acetyl-L-leucine | 3 | 2 | 2 | 3 | 2 | 2 | 14 | 3 | 2 | 2 | 3 | 2 |
| D + N-acetyl-L-serine | 3 | 2 | 2 | 2 | 2 | 2 | 13 | 3 | 2 | 2 | 3 | 2 |
| D + N-acetyl-L-proline | 3 | 2 | 1 | 3 | 2 | 2 | 13 | 2 | 3 | 2 | 3 | 2 |
| D + N-acetyl-L-tryptophan | 1 | 1 | 1 | 0 | 1 | 1 | 5 | 0 | 1 | 1 | 1 | 0 |
| D + N-acetyl-L-isoleucine | 3 | 2 | 3 | 3 | 1 | 3 | 15 | 2 | 2 | 2 | 3 | 2 |
| D + N-acetyl-L-glutamic acid | 3 | 2 | 2 | 2 | 2 | 3 | 14 | 2 | 2 | 2 | 3 | 2 |
| D + N-acetyl-L-glycine | 3 | 2 | 2 | 2 | 2 | 3 | 14 | 3 | 2 | 2 | 3 | 2 |

TABLE 1-continued

| | | | | | | | | | | | | |
|---|---|---|---|---|---|---|---|---|---|---|---|---|
| D + N-acetyl-L-valine | 3 | 2 | 2 | 2 | 2 | 3 | 14 | 2 | 2 | 2 | 2 | 2 |
| D + N-acetyl-L-arginine | 1 | 1 | 1 | 1 | 1 | 1 | 6 | 1 | 1 | 1 | 1 | 1 |
| D + N-acetyl-L-Lysine | 3 | 2 | 2 | 3 | 2 | 1 | 13 | 3 | 3 | 2 | 2 | 2 |
| D + N-acetyl-L-tyrosine | 3 | 2 | 3 | 3 | 2 | 2 | 15 | 3 | 2 | 2 | 3 | 2 |
| D + N-acetyl-L-glutamine | 2 | 2 | 2 | 2 | 2 | 3 | 13 | 2 | 2 | 2 | 2 | 2 |
| D + N-acetyl-L-histidine | 3 | 2 | 2 | 3 | 2 | 3 | 15 | 3 | 2 | 2 | 3 | 2 |
| D + N-acetyl-L-methionine | 2 | 2 | 2 | 3 | 2 | 3 | 14 | 3 | 2 | 3 | 3 | 2 |

| | Mouse 2 | | Mouse 3 | | | | | | | | |
|---|---|---|---|---|---|---|---|---|---|---|---|
| | Licheni-fication | Sum | Erythema | Edema | Eschar | Dryness | Abrasion | Licheni-fication | Sum | Mean | Deviation |
| Control | 0 | 0 | 0 | 0 | 0 | 0 | 0 | 0 | 0 | | |
| DNFB (D) | 3 | 15 | 3 | 3 | 2 | 2 | 3 | 3 | 16 | 15.33 | 0.58 |
| D + N-acetyl-L-cysteine | 3 | 13 | 1 | 2 | 2 | 2 | 2 | 2 | 11 | 12.33 | 1.15 |
| D + N-acetyl-L-alanine | 0 | 4 | 1 | 1 | 1 | 0 | 1 | 1 | 5 | 5 | 1 |
| D + N-acetyl-L-asparagine | 3 | 14 | 3 | 3 | 3 | 3 | 2 | 2 | 16 | 15 | 1 |
| D + N-acetyl-L-phenylalanine | 3 | 15 | 3 | 2 | 2 | 3 | 1 | 3 | 14 | 14 | 1 |
| D + N-acetyl-L-aspartic acid | 2 | 14 | 3 | 2 | 2 | 2 | 2 | 1 | 12 | 13 | 1 |
| D + N-acetyl-L-threonine | 1 | 5 | 1 | 1 | 2 | 1 | 0 | 1 | 6 | 6 | 1 |
| D + N-acetyl-L-leucine | 3 | 15 | 3 | 2 | 2 | 3 | 2 | 1 | 13 | 14 | 1 |
| D + N-acetyl-L-serine | 3 | 15 | 3 | 2 | 2 | 3 | 2 | 2 | 14 | 14 | 1 |
| D + N-acetyl-L-proline | 2 | 14 | 3 | 2 | 2 | 3 | 1 | 2 | 13 | 13.33 | 0.58 |
| D + N-acetyl-L-tryptophan | 0 | 3 | 0 | 0 | 2 | 0 | 2 | 0 | 4 | 4 | 1 |
| D + N-acetyl-L-isoleucine | 3 | 14 | 3 | 2 | 2 | 3 | 1 | 3 | 14 | 14.33 | 0.58 |
| D + N-acetyl-L-glutamic acid | 2 | 13 | 1 | 2 | 2 | 3 | 2 | 2 | 12 | 13 | 1 |
| D + N-acetyl-L-glycine | 3 | 15 | 3 | 2 | 2 | 3 | 2 | 3 | 15 | 14.67 | 0.58 |
| D + N-acetyl-L-valine | 3 | 13 | 2 | 2 | 2 | 3 | 1 | 2 | 12 | 13 | 1 |
| D + N-acetyl-L-arginine | 1 | 6 | 1 | 1 | 1 | 1 | 0 | 1 | 5 | 5.67 | 0.58 |
| D + N-acetyl-L-Lysine | 3 | 15 | 3 | 2 | 2 | 3 | 2 | 2 | 14 | 14 | 1 |
| D + N-acetyl-L-tyrosine | 3 | 15 | 3 | 2 | 2 | 2 | 2 | 2 | 13 | 14.33 | 1.15 |
| D + N-acetyl-L-glutamine | 2 | 12 | 2 | 2 | 2 | 2 | 2 | 1 | 11 | 12 | 1 |
| D + N-acetyl-L-histidine | 3 | 15 | 3 | 2 | 2 | 3 | 2 | 2 | 14 | 14.67 | 0.58 |
| D + N-acetyl-L-methionine | 3 | 16 | 2 | 2 | 2 | 3 | 2 | 3 | 14 | 14.67 | 1.15 |

Figure 2A:
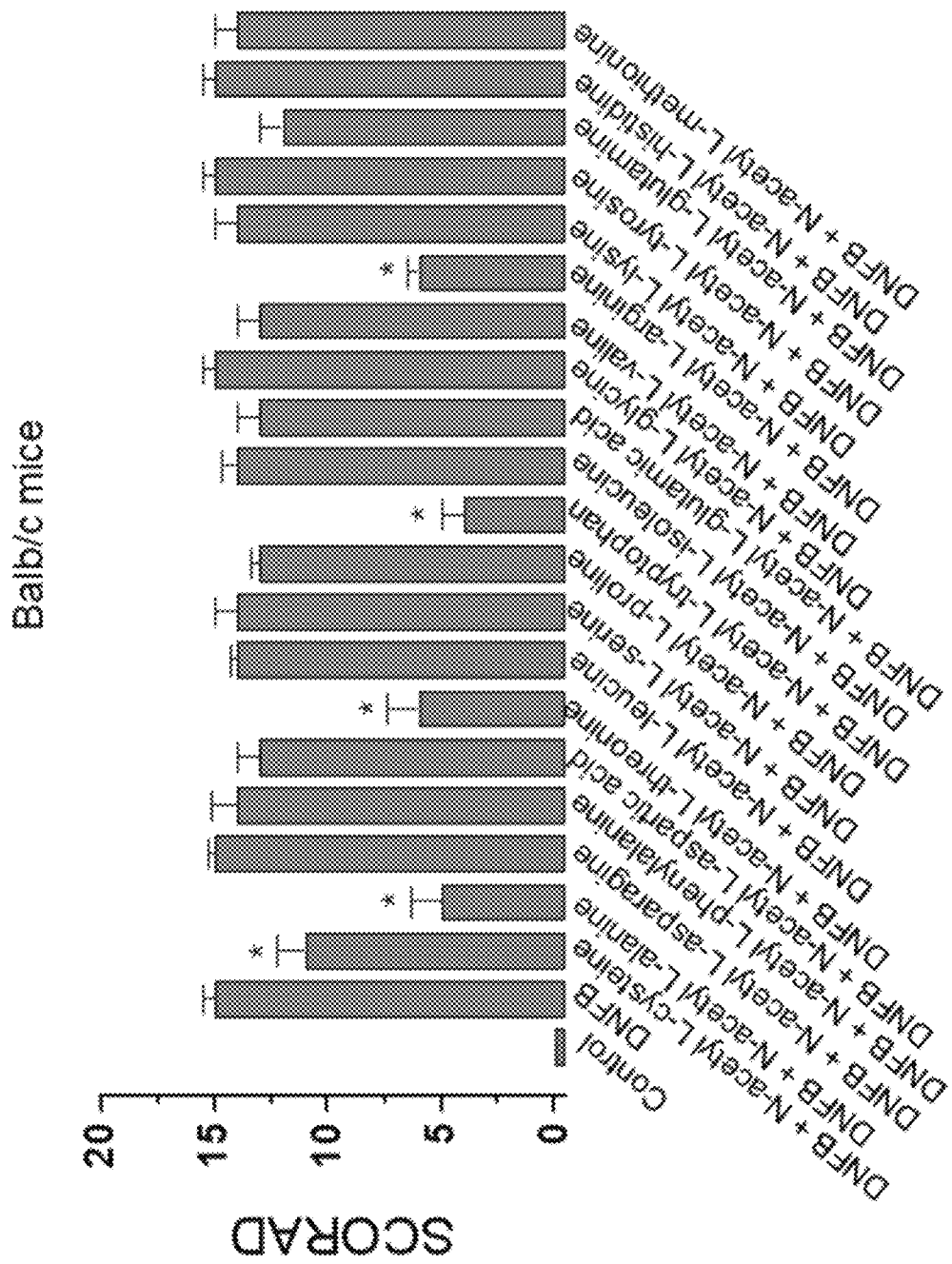
FIG. 2A shows a result of applying 20 N-acetyl-L-amino acids on the dermatitis-induced area of atopic dermatitis-induced Balb/c mouse and then measuring clinical skin scores (SCORAD) (*P<0.05 versus 2,4-dinitrofluorobenzene (DNFB)-treated group).
Figure 2B:
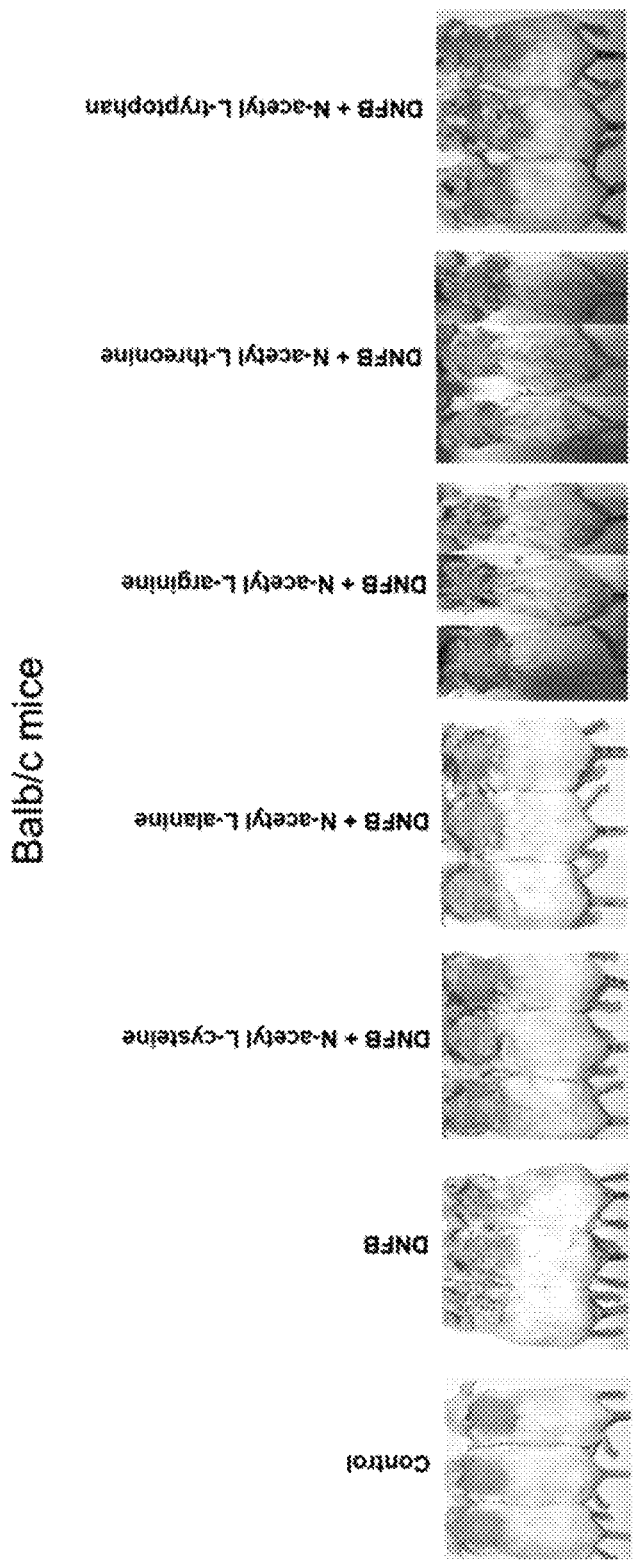
FIG. 2B shows the images of the back skin of Balb/c mouse treated with 2,4-dinitrofluorobenzene (DNFB) to induce atopic dermatitis and then treated for 7 days with a control substance, N-acetyl-L-cysteine, N-acetyl-L-alanine, N-acetyl-L-threonine, N-acetyl-L-arginine or N-acetyl-L-tryptophan on day 29.

Also, as seen from FIG. 2A, from among the 20 N-acetyl-L-amino acids, N-acetyl-L-cysteine, N-acetyl-L-alanine, N-acetyl-L-arginine, N-acetyl-L-threonine and N-acetyl-L-tryptophan showed significant atopic dermatitis-treating effect in the Balb/c atopic dermatitis model (FIG. 2A). The apparent degree of dermatitis was also decreased remarkably in the atopy-induced mice treated with N-acetyl-L-cysteine, N-acetyl-L-alanine, N-acetyl-L-arginine, N-acetyl-L-threonine or N-acetyl-L-tryptophan (FIG. 2B).

Figure 3A:
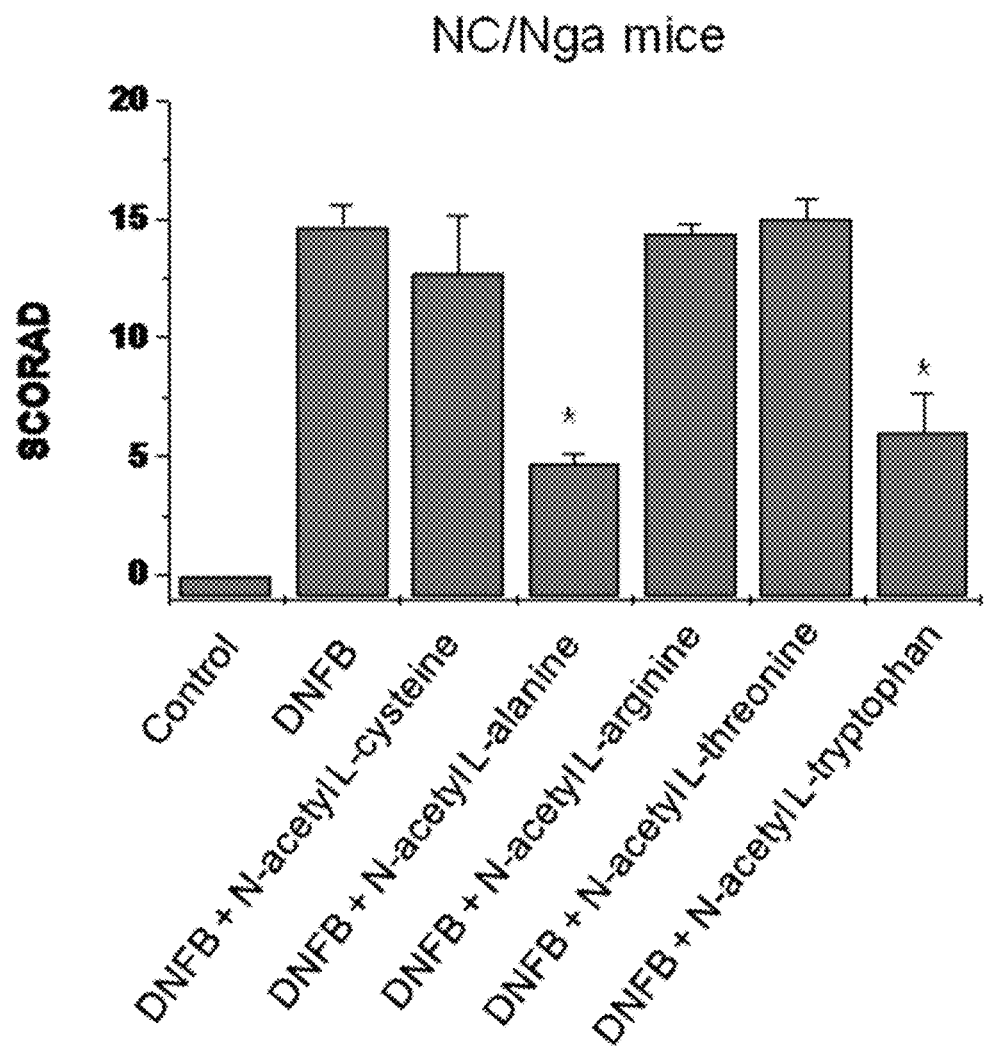
FIG. 3A shows a result of applying N-acetyl-L-cysteine, N-acetyl-L-alanine, N-acetyl-L-threonine, N-acetyl-L-arginine or N-acetyl-L-tryptophan on the dermatitis-induced area of atopic dermatitis-induced Nc/Nga mouse and then measuring clinical skin scores (SCORAD) (*P<0.05 versus 2,4-dinitrofluorobenzene (DNFB)-treated group).
Figure 3B:
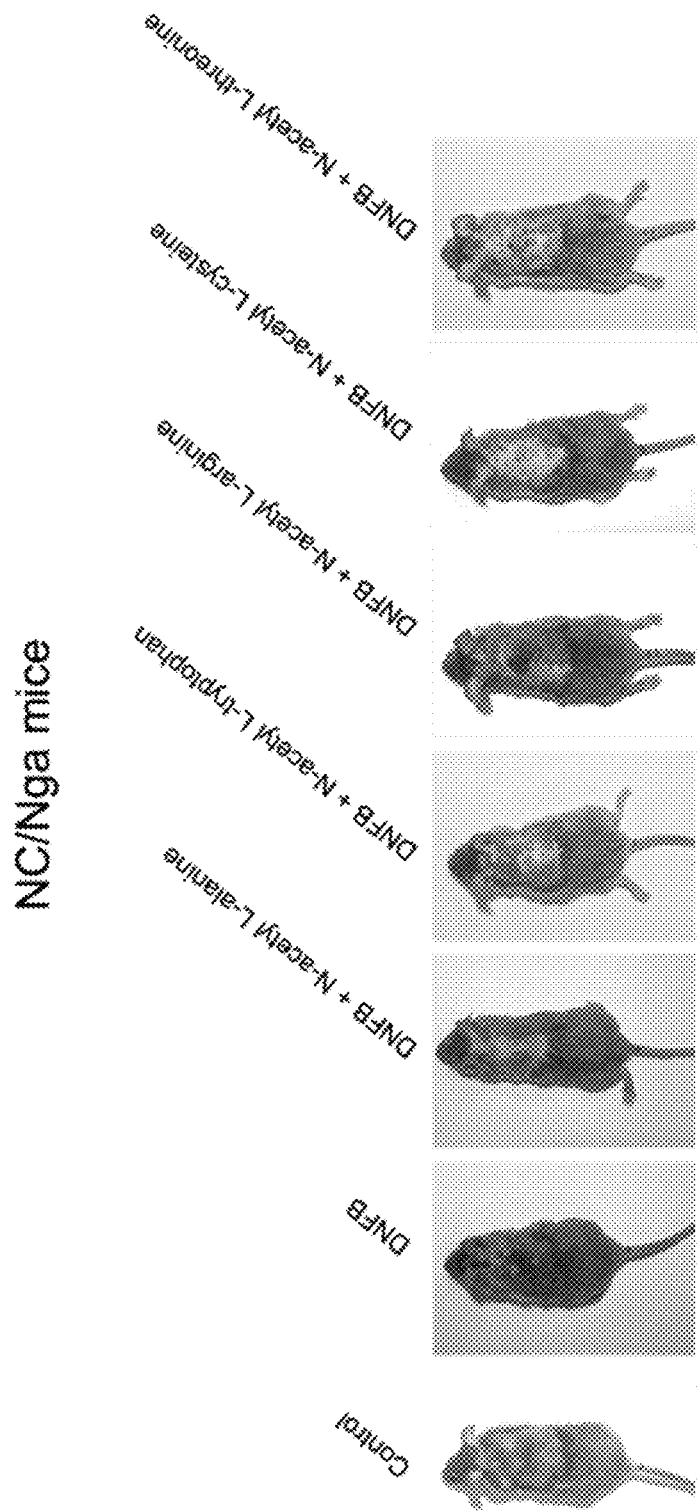
FIG. 3B shows the images of the back skin of Nc/Nga mouse treated with 2,4-dinitrofluorobenzene (DNFB) to induce atopic dermatitis and then treated for 7 days with a control substance, N-acetyl-L-cysteine, N-acetyl-L-alanine, N-acetyl-L-threonine, N-acetyl-L-arginine or N-acetyl-L-tryptophan on day 22.
Figure 3C:
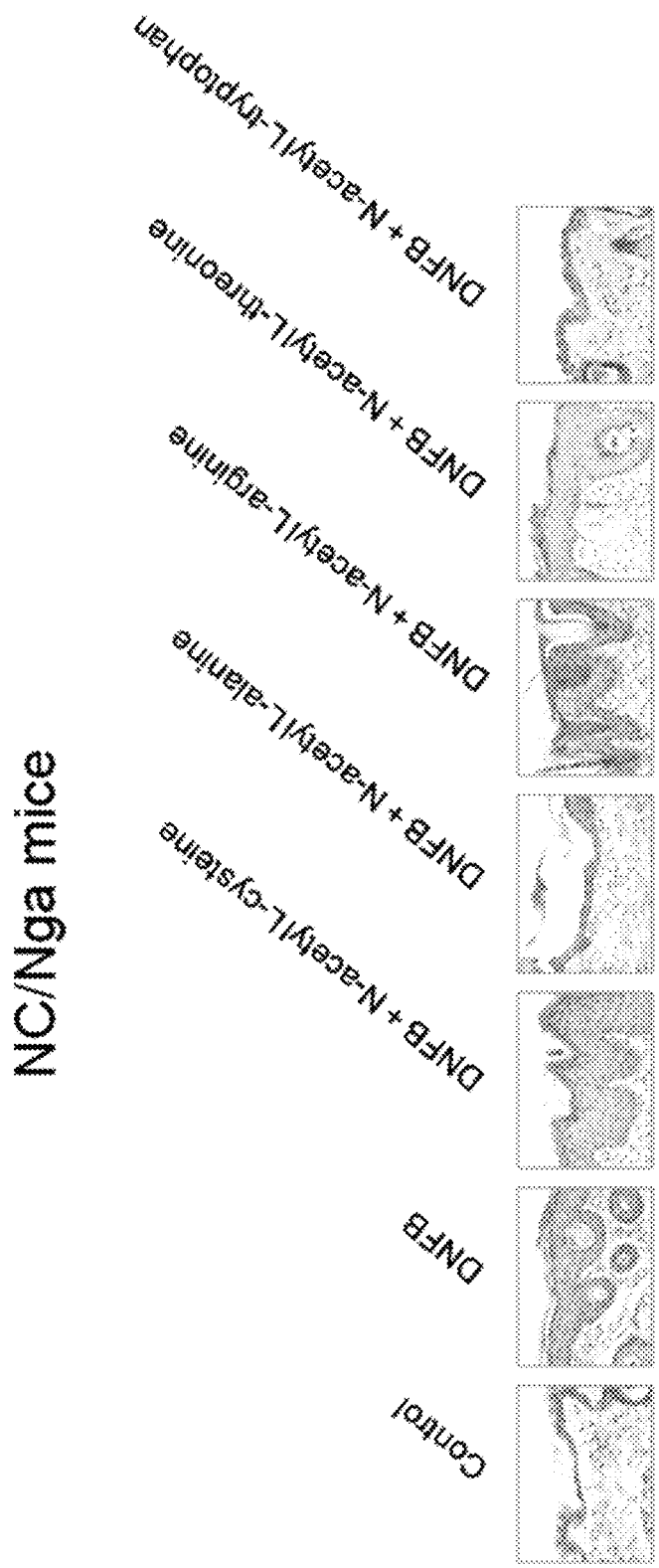
FIG. 3C shows a result of treating Nc/Nga mouse with 2,4-dinitrofluorobenzene (DNFB) to induce atopic dermatitis, treating for 7 days with a control substance, N-acetyl-L-cysteine, N-acetyl-L-alanine, N-acetyl-L-threonine, N-acetyl-L-arginine or N-acetyl-L-tryptophan on day 22, and then staining the back skin tissue sliced to a thickness of 5 μm with hematoxylin/eosin.

As seen from FIG. 3, from among the N-acetyl-L-cysteine, N-acetyl-L-alanine, N-acetyl-L-arginine, N-acetyl-L-threonine and N-acetyl-L-tryptophan, which exhibited effects in the Balb/c atopic dermatitis model, N-acetyl-L-alanine and N-acetyltryptophan showed atopic dermatitis-treating effect in the atopic dermatitis model of Nc/Nga mice (FIG. 3A). Nc/Nga mice are widely used as an atopic dermatitis model. In particular, N-acetyl-L-alanine and N-acetyltryptophan showed remarkable effect in this model (FIG. 3B). After extracting back skin tissues of the atopic dermatitis-induced and drug-treated Nc/Nga mice of Example 2, the tissues were fixed with an Accustain formalin-free fixative solution and then prepared into paraffin blocks. The paraffin blocks were sliced to a thickness of 5 μm and the change in the thickness of the epidermal and dermal layers was observed by staining with hematoxylin/eosin. The thickness of the epidermal and dermal layers, which was increased by the induction of atopic dermatitis, was significantly decreased by the treatment with N-acetyl-L-alanine or N-acetyl-L-tryptophan (FIG. 3C).

<Example 5> Measurement of Serum IqE Level

Figure 4A:
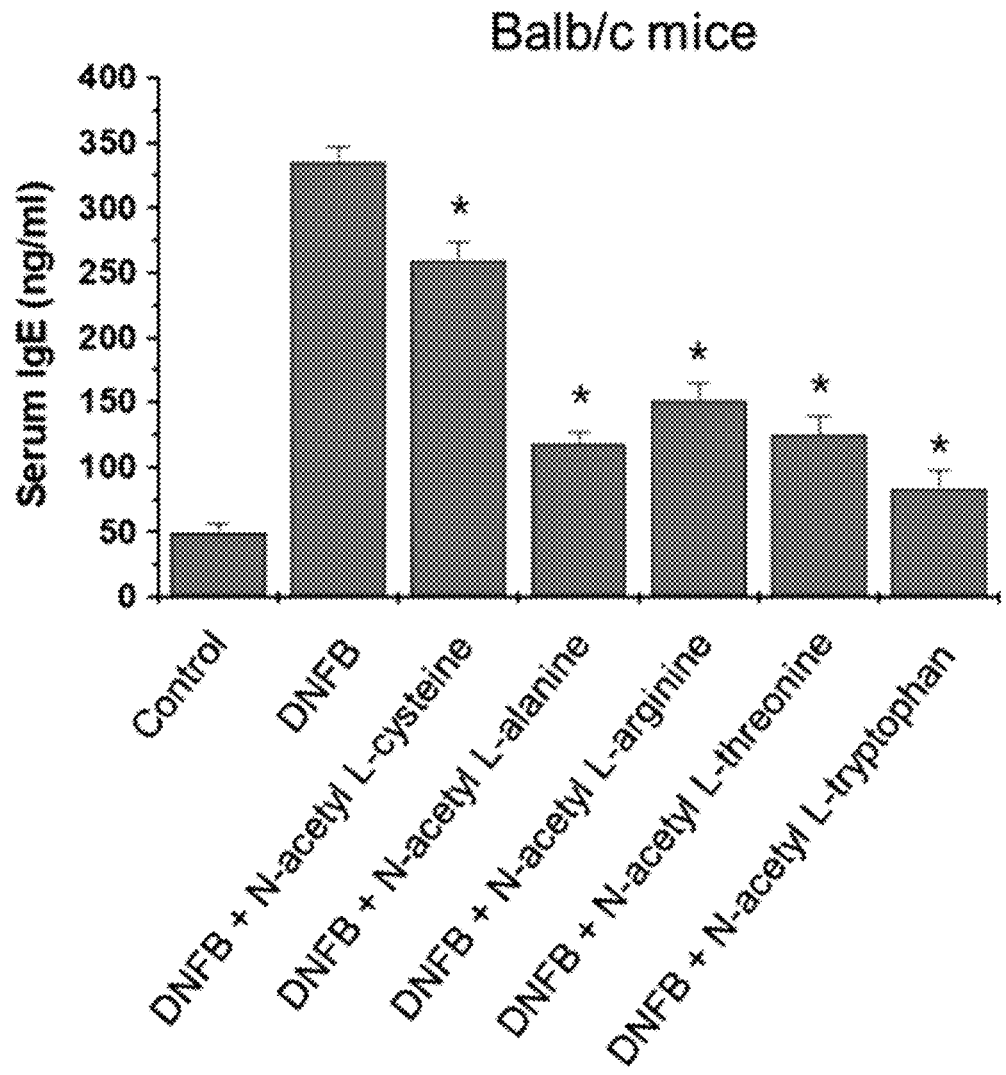
FIG. 4A shows a result of treating Balb/c mouse with 2,4-dinitrofluorobenzene (DNFB) to induce atopic dermatitis, treating for 7 days with a control substance, N-acetyl-L-cysteine, N-acetyl-L-alanine, N-acetyl-L-threonine, N-acetyl-L-arginine or N-acetyl-L-tryptophan on day 29, and then measuring the total IgE level in the serum sample of the mouse by ELISA (*P<0.05 versus 2,4-dinitrofluorobenzene (DNFB)).
Figure 4B:
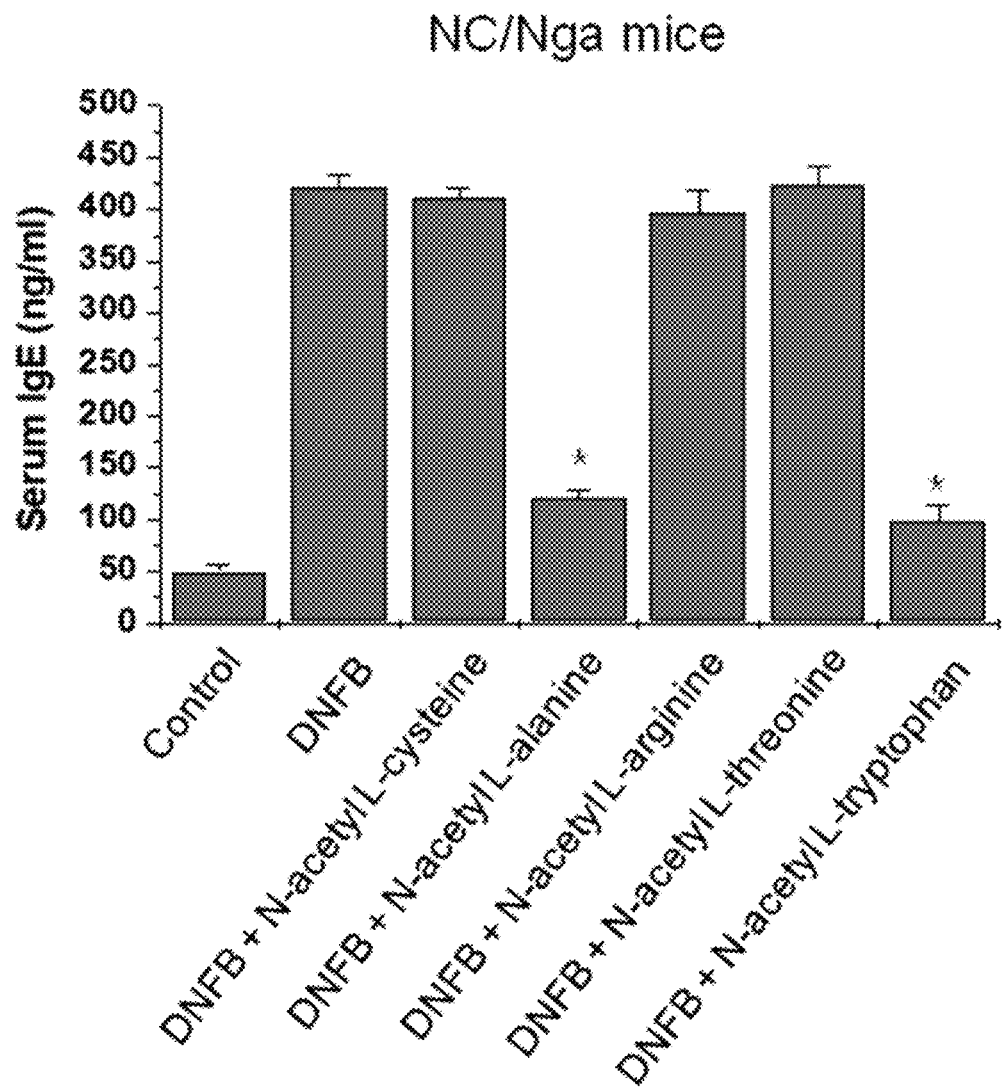
FIG. 4B shows a result of treating Nc/Nga mouse with 2,4-dinitrofluorobenzene (DNFB) to induce atopic dermatitis, treating for 7 days with a control substance, N-acetyl-L-cysteine, N-acetyl-L-alanine, N-acetyl-L-threonine, N-acetyl-L-arginine or N-acetyl-L-tryptophan on day 29, and then measuring the total IgE level in the serum sample of the mouse by ELISA (*P<0.05 versus 2,4-dinitrofluorobenzene (DNFB)).

After treatment with the test substance, the mice were sacrificed and blood was taken from the heart. After isolating serum from the blood, IgE level was measured. Specifically, after attaching antibodies diluted in a buffer solution onto a 96-well plate and incubating overnight at 4° C., experiment was conducted using an IgE ELISA kit (BD Biosciences, San Diego, CA) according to the provided manual. The quantity of the IgE protein was determined by measuring absorbance at 450 nm using a microplate reader. As seen from FIGS. 4A-4B, the treatment of the atopy-induced Balb/c mice with N-acetyl-L-cysteine, N-acetyl-L-alanine, N-acetyl-L-arginine, N-acetyl-L-threonine and N-acetyl-L-tryptophan resulted in significant decrease in serum IgE level (FIG. 4A), and the treatment of the atopy-induced Nc/Nga mice with N-acetyl-L-alanine and N-acetyl-L-tryptophan resulted in significant decrease in serum IgE level (FIG. 4B). Because the serum IgE level is indicative of the severity of atopic dermatitis, the result of FIGS. 4A-4B shows that N-acetyl-L-alanine, N-acetyl-L-arginine, N-acetyl-L-threonine and N-acetyl-L-tryptophan have atopic dermatitis-treating effect.

<Example 6> Measurement of IL4 and Interferon γ by Quantitative Real-time PCR

Figure 5A:
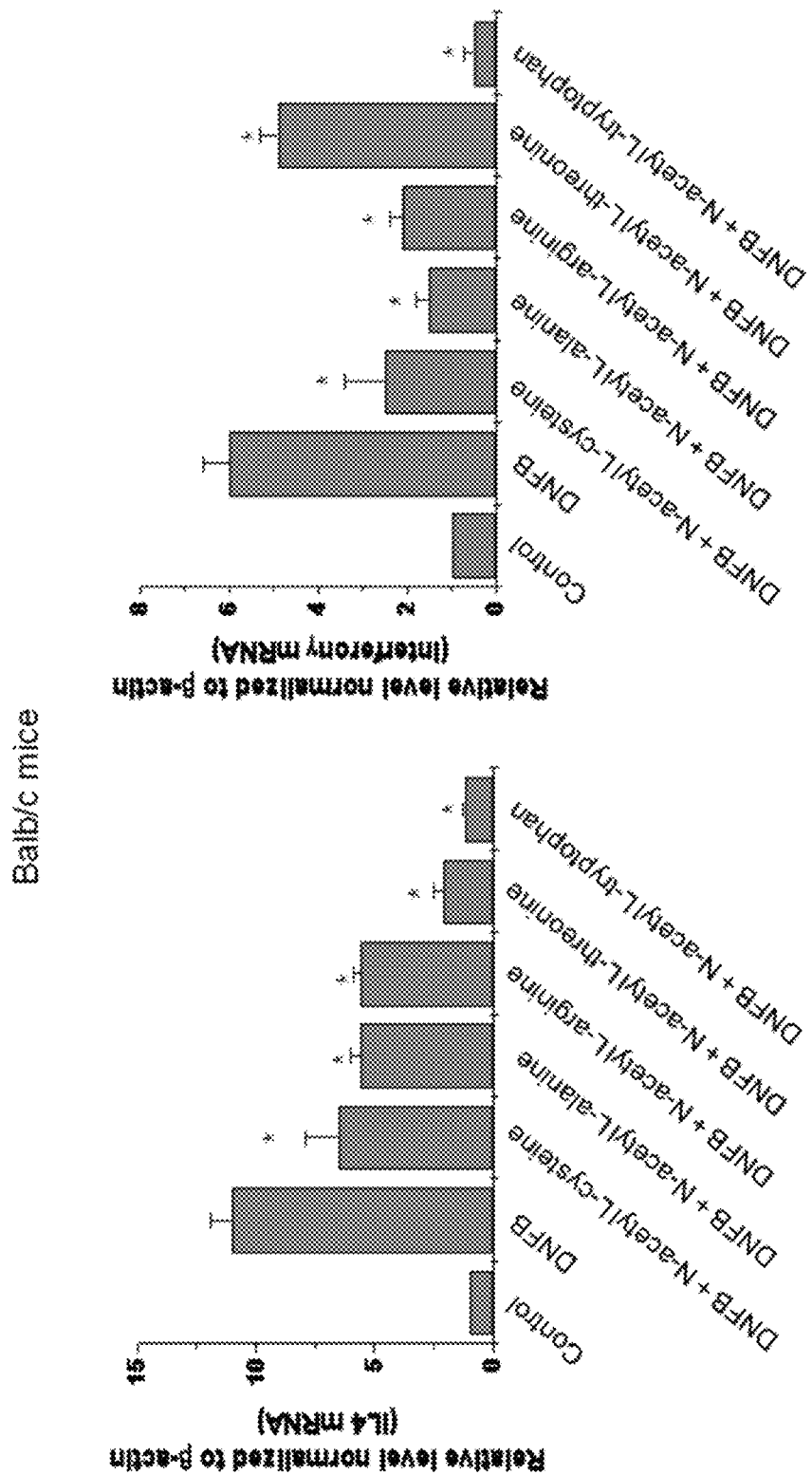
FIG. 5A shows a result of treating Balb/c mouse with 2,4-dinitrofluorobenzene (DNFB) to induce atopic dermatitis, treating for 7 days with a control substance, N-acetyl-L-cysteine, N-acetyl-L-alanine, N-acetyl-L-threonine, N-acetyl-L-arginine or N-acetyl-L-tryptophan on day 29, and then measuring the quantity of IL4 and interferon γ mRNAs in the skin tissue of the mouse (*P<0.05 versus 2,4-dinitrofluorobenzene (DNFB)).
Figure 5B:
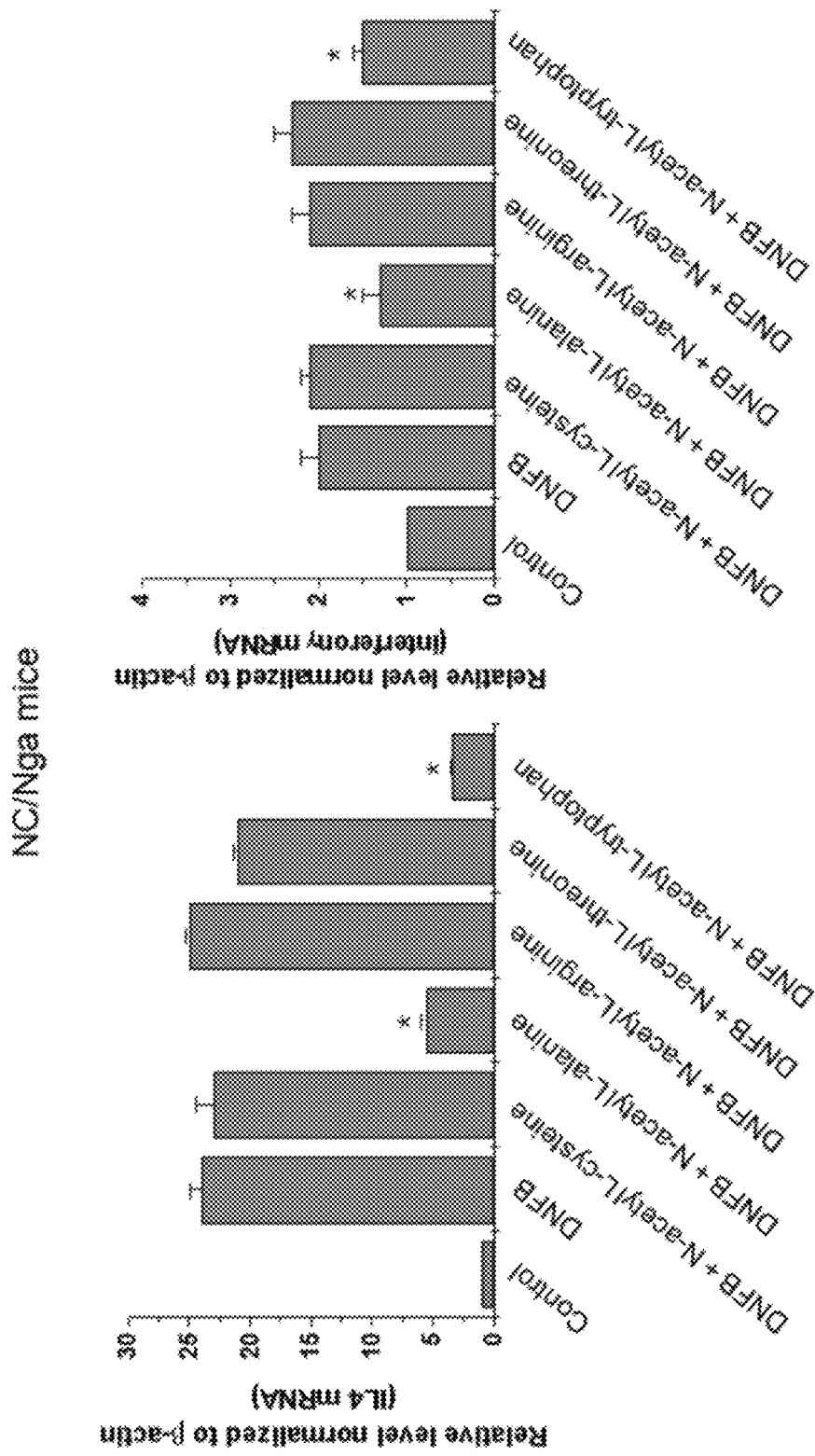
FIG. 5B shows a result of treating Nc/Nga mouse with 2,4-dinitrofluorobenzene (DNFB) to induce atopic dermatitis, treating for 7 days with a control substance, N-acetyl-L-cysteine, N-acetyl-L-alanine, N-acetyl-L-threonine, N-acetyl-L-arginine or N-acetyl-L-tryptophan on day 29, and then measuring the quantity of IL4 and interferon γ mRNAs in the skin tissue of the mouse (*P<0.05 versus 2,4-dinitrofluorobenzene (DNFB)).

After isolating total RNA from the atopy-induced skin tissue using 500 µL of Trizol (Life Technologies, USA) according to the manufacturer's protocol and synthesizing cDNA using the Superscript III reverse transcriptase (Life Technologies, USA), real-time PCR was conducted by reacting with the primers of IL4 and interferon γ to be analyzed. The real-time PCR was conducted on a StepOne Plus PCR cycler (Applied Biosystems) using SYBR Green (Applied Biosystems, Foster City, CA). The mRNA expression data were analyzed by the ΔΔCT method and were normalized to β-actin for gene detection. The primers necessary for the real-time PCR were purchased from Qiagen (USA). As seen from FIGS. 5A-5B, the treatment of the atopy-induced Balb/c mice with N-acetyl-L-cysteine, N-acetyl-L-alanine, N-acetyl-L-arginine, N-acetyl-L-threonine and N-acetyl-L-tryptophan significantly decreased the level of IL4 and interferon γ in the skin tissue (FIG. 5A), and the treatment of the atopy-induced Nc/Nga mice with N-acetyl-L-alanine and N-acetyl-L-tryptophan significantly decreased the level of IL4 and interferon γ in the skin tissue. IL4 is known to induce TH2 response and interferon γ is known to induce TH1 response. Accordingly, the result of FIGS. 5A-5B shows that N-acetyl-L-alanine, N-acetyl-L-arginine, N-acetyl-L-threonine and N-acetyl-L-tryptophan exhibit therapeutic effects by inhibiting TH2 and TH1 responses activated by atopic dermatitis.

<Example 7> Stereo-Specificity of N-Acetylamino Acid

Figure 6:
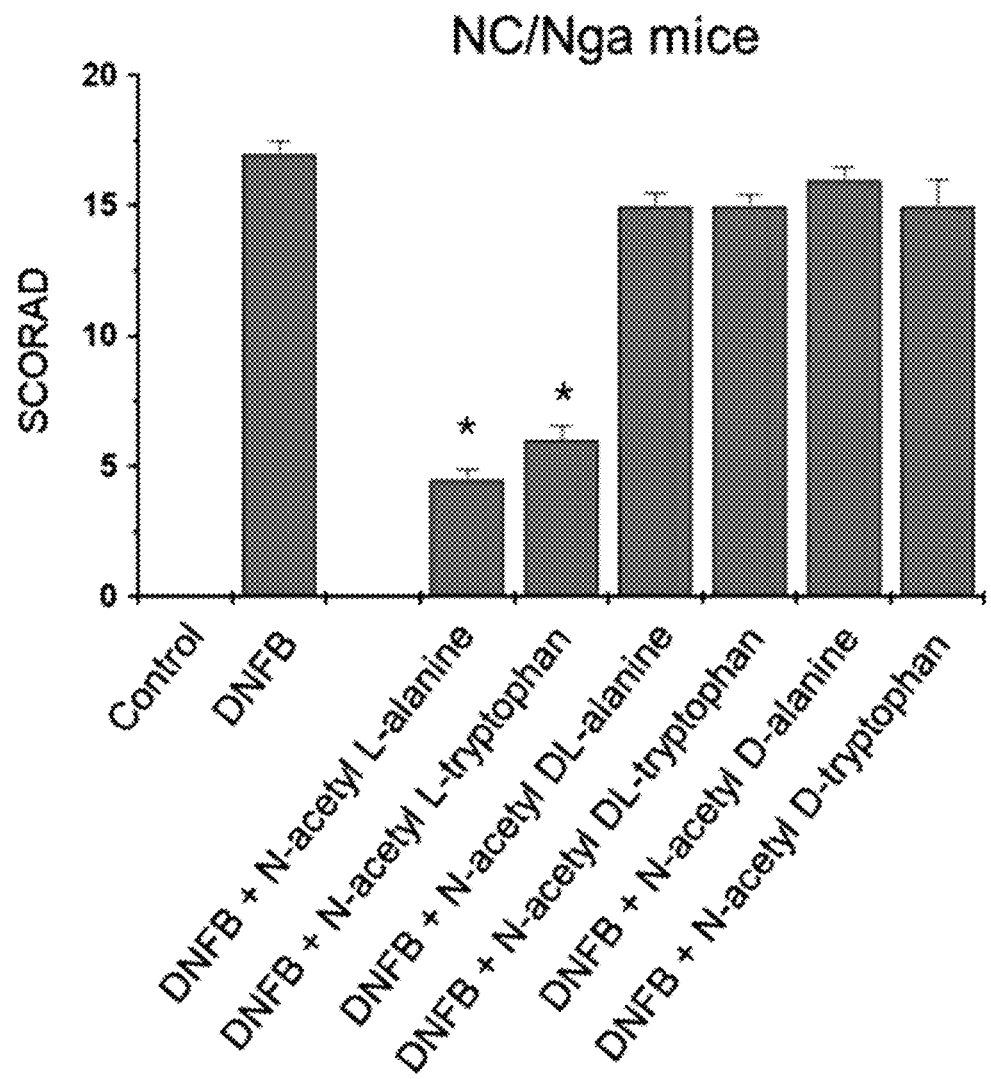
FIG. 6 shows a result of comparing the atopic dermatitis-relieving effect of L-form N-acetylalanine and N-acetyltryptophan with D/L-form and D-form N-acetylalanine and N-acetyltryptophan at a concentration of 0.1% in Nc/Nga mouse in which atopic dermatitis is induced with DNFB (*P<0.05 versus 2,4-dinitrofluorobenzene (DNFB)).

In order to investigate the effect of L-form, L/D-form and D-form N-acetylalanine and N-acetyltryptophan on atopic dermatitis, their dermatitis-treating effect was evaluated for the atopic dermatitis model of Nc/Nga mice. As a result, the L/D-form and D-form N-acetylalanine and N-acetyltryptophan had no effect and only the L-form showed remarkable effect (FIG. 6). This shows that the pruritus-inhibiting action by these substances is stereo-specific.

<Example 8> Pruritus Inhibition Test

Figure 7:
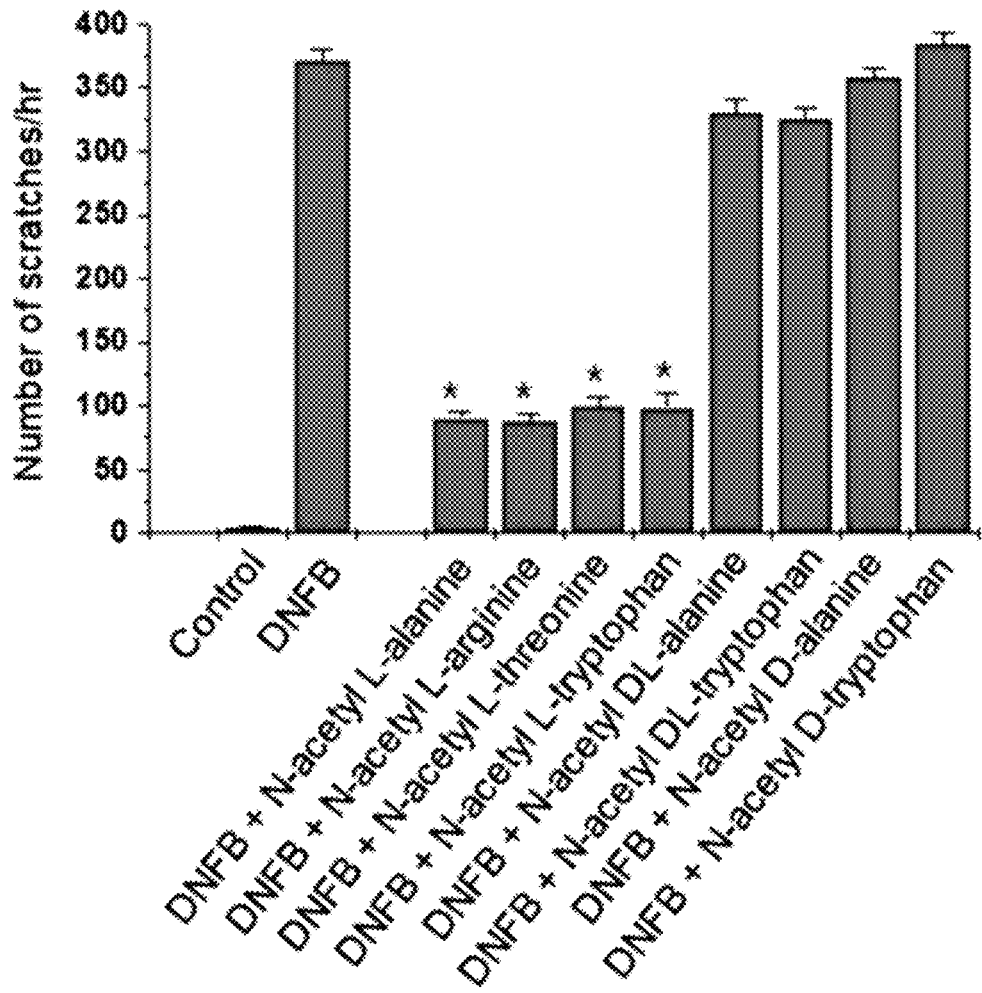
FIG. 7 shows a result of comparing the pruritus-relieving effect of L-form N-acetylalanine, N-acetylthreonine, N-acetylarginine and N-acetyltryptophan with D/L-form and D-form N-acetylalanine and N-acetyltryptophan at a concentration of 0.1% in Nc/Nga mouse in which atopic dermatitis is induced with DNFB (*P<0.05 versus 2,4-dinitrofluorobenzene (DNFB)).

In order to investigate whether L-form, L/D-form and D-form N-acetylalanine, N-acetylarginine, N-acetylthreonine and N-acetyltryptophan inhibit pruritus caused by atopic contact dermatitis, 20 µL of 0.1% 2,4-dinitrofluorobenzene (DNFB) solution and 0.1% N-acetylamino acid dissolved in physiological saline were applied once onto the right ear 10 minutes after the final treatment (day 27) with 2,4-dinitrofluorobenzene (DNFB) (Physiological saline was applied to a negative control group), and then pruritus was measured for 1 hour. FIG. 7 compares the pruritus-relieving effect of L-form N-acetylalanine, N-acetylthreonine, N-acetylarginine and N-acetyltryptophan with D/L-form and D-form N-acetylalanine and N-acetyltryptophan at 0.1% after the induction of pruritus with DNFB. The L-form N-acetylalanine, N-acetylthreonine, N-acetylarginine and N-acetyltryptophan significantly inhibited pruritus, whereas the D/L-form and D-form N-acetylalanine and N-acetyltryptophan had little effect. This result shows that the pruritus-inhibiting action by these substances is stereo-specific.

<Example 9> Synthesis of Acyl Derivatives of Tryptophan

In order to evaluate the effect of N-acyltryptophan compounds other than N-acetyltryptophan, N-propionyltryptophan, N-butyltryptophan, N-pentanoyltryptophan, N-undecanoyltryptophan, N-palmitoyltryptophan, N—(Z)-docos-13-enoyltryptophan and N-stearoyltryptophan, N-oleoyltryptophan were synthesized according to the reaction scheme described below. The reagents used in this example were purchased from Sigma-Aldrich (USA), TCI (Japan), Alfa Aesar (USA), Acros (USA), Hanawa (Japan), etc. and used without purification. The purity of the synthesized compounds and the progress of reaction were identified by thin layer chromatography (TLC) using the PLC Silica gel 60 F254, 0.5 mm (Merck). The substances separated by TLC were identified using UV lamps (254 nm, 365 nm). Separation was conducted by medium-pressure liquid chromatography (MPLC) using a silica gel column cartridge (4-120 g, RediSep Rf) and PLC2020 (Gilson) or by high-performance liquid chromatography (HPLC) using an Agilent 5 Prep-C18 100×21.2 mm column, a YL9100 Semi-prep HPLC system (YL9101S vacuum degasser, YL9111S binary pump, YL9120S UV/Vis detector; Young Lin Instrument). Mass analysis of the products was conducted with Agilent 6130 Quadrupole LC/MS. The NMR spectra for structural analysis of the products were measured with a Bruker ultra-shield 300 MHz NMR spectrometer and a Bruker ultra-shield 500 MHz NMR Spectrometer. Chloroform-d and dimethylsulfoxide-$d_6$ (Cambridge Isotope Laboratories) were used as NMR solvents and tetramethylsilane (TMS) was used as an internal standard. The NMR data were presented in ppm units.

(Reaction scheme)

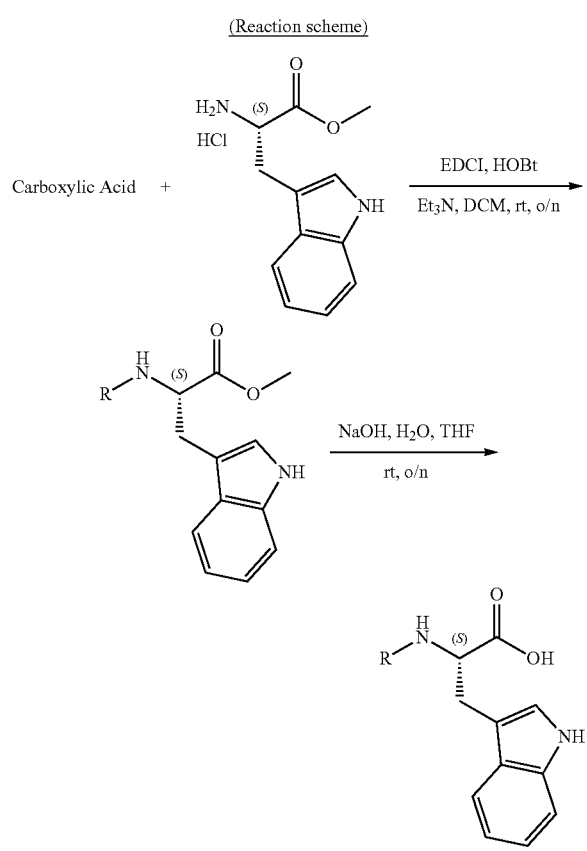

<Example 9-1> Preparation of N-propionyltryptophan

First, for preparation of methylpropionyl L-tryptophanate, a mixture of propionic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated $NaHCO_3$ solution, and then extracted 3 times with ethyl acetate. The extracted organic solvent layer was combined, washed with brine, washed with 1 N HCl, and then washed again with brine. The organic solvent layer was dried on anhydrous $MgSO_4$, concentrated and then purified by medium-pressure liquid chromatography (MPLC) using n-hexane and ethyl acetate. The yield was 74% and the characteristics of the methylpropionyl L-tryptophanate are as follows. $^1$HNMR (500 MHz, chloroform-d) δ 8.19 (s, 1H), 7.61-7.53 (m, 1H), 7.39 (dt, J=8.2, 0.9 Hz, 1H), 7.22 (ddd, J=8.2, 7.0, 1.2 Hz, 1H), 7.16-7.07 (m, 1H), 7.00 (d, J=2.4 Hz, 1H), 6.04-5.88 (m, 1H), 5.00 (dt, J=7.9, 5.3 Hz, 1H), 3.73 (s, 3H), 3.44-3.29 (m, 2H), 2.21 (qd, J=7.6, 1.2 Hz, 2H), 1.14 (t, J=7.6 Hz, 3H). LC-MS (ESI), calcd for $C_{15}H_{18}N_2O_3$ 274.1, found m/z 275.1 (M+H$^+$).

In order to prepare N-propionyltryptophan from the methylpropionyl-L-tryptophanate, a NaOH (1.48 mmol) solution was added to the methylpropionyl-L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous $MgSO_4$ and then concentrated. The yield was 92% and the characteristics of the N-propionyltryptophan are as follows. $^1$H NMR (500 MHz, DMSO-d$_6$) δ 10.82 (d, J=2.4 Hz, 1H), 8.03 (d, J=7.9 Hz, 1H), 7.53 (d, J=7.9 Hz, 1H), 7.35-7.27 (m, 1H), 7.13 (d, J=2.3 Hz, 1H), 7.06 (ddd, J=8.1, 6.9, 1.2 Hz, 1H), 6.98 (ddd, J=8.0, 6.9, 1.1 Hz, 1H), 4.46 (d, J=4.8 Hz, 1H), 3.15 (d, J=5.0 Hz, 1H), 3.01 (d, J=8.8 Hz, 1H), 2.08 (qd, J=7.5, 3.1 Hz, 2H), 0.94 (d, J=7.6 Hz, 3H). LC-MS (ESI), calcd for $C_{14}H_{16}N_2O_3$ 260.1, found m/z 261.1 (M+H$^+$).

<Example 9-2> Preparation of N-butyryltryptophan

First, for preparation of methylbutyryl L-tryptophanate, butyric acid (2.36 mmol), a mixture of L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated $NaHCO_3$ solution, and then extracted 3 times with ethyl acetate. The extracted organic solvent layer was combined, washed with brine, washed with 1 N HCl, and then washed again with brine. The organic solvent layer was dried on anhydrous $MgSO_4$, concentrated, and then purified by medium-pressure liquid chromatography (MPLC) using n-hexane and ethyl acetate. The yield was 83% and the characteristics of the methylbutyryl L-tryptophanate are as follows. $^1$H NMR (500 MHz, chloroform-d) δ 8.15 (s, 1H), 7.61-7.51 (m, 1H), 7.39 (dt, J=8.1, 0.9 Hz, 1H), 7.22 (ddd, J=8.1, 7.0, 1.1 Hz, 1H), 7.15 (ddd, J=8.0, 7.0, 1.0 Hz, 1H), 7.01 (d, J=2.4 Hz, 1H), 5.98 (d, J=7.9 Hz, 1H), 5.01 (dt, J=7.9, 5.3 Hz, 1H), 3.73 (s, 3H), 3.39-3.29 (m, 2H), 2.16 (t, J=7.5 Hz, 2H), 1.70-1.58 (m, 3H), 0.93 (t, J=7.4 Hz, 3H). LC-MS (ESI), calcd for $C_{16}H_{20}N_2O_3$ 288.2, found m/z 289.2 (M+H$^+$).

In order to prepare N-butyryltryptophan from the methylbutyryl L-tryptophanate, a NaOH (1.48 mmol) solution was added to the methylbutyryl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous $MgSO_4$ and then concentrated. The yield was 94% and the characteristics of the N-butyryltryptophan are as follows. $^1$H NMR (500 MHz, chloroform-d) δ 8.30 (s, 1H), 7.60 (d, J=8.1 Hz, 1H), 7.38 (dt, J=8.2, 0.9 Hz, 1H), 7.22 (ddd, J=8.1, 7.0, 1.2 Hz, 1H), 7.14 (ddd, J=8.0, 7.1, 1.0 Hz, 1H), 7.04 (d, J=2.3 Hz, 1H), 6.08 (d, J=7.6 Hz, 1H), 4.95 (dd, J=7.6, 5.4 Hz, 1H), 3.44-3.32 (m, 2H), 2.11-2.08 (m, 2H), 1.58 (q, J=7.4 Hz, 2H), 0.87 (t, J=7.4 Hz, 3H). LC-MS (ESI), calcd for $C_{15}H_{18}N_2O_3$ 274.1, found m/z 275.1 (M+H$^+$).

<Example 9-3> Preparation of N-pentanoyltryptophan

First, for preparation of methylpentanoyl L-tryptophanate, a mixture of pentanoic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution, and then extracted 3 times with ethyl acetate. The extracted organic solvent layer was combined, washed with brine, washed with 1 N HCl, and then washed again with brine. The organic solvent layer was dried on anhydrous MgSO$_4$, concentrated, and then purified by medium-pressure liquid chromatography (MPLC) using n-hexane and ethyl acetate. The yield was 85% and the characteristics of the methylpentanoyl L-tryptophanate are as follows. $^1$H NMR (500 MHz, chloroform-d) δ 8.14 (s, 1H), 7.56 (dt, J=8.0, 1.0 Hz, 1H), 7.39 (dd, J=8.1, 0.9 Hz, 1H), 7.22 (ddd, J=8.2, 7.0, 1.2 Hz, 1H), 7.15 (ddd, J=8.0, 7.1, 1.0 Hz, 1H), 7.01 (d, J=2.4 Hz, 1H), 5.97 (d, J=8.0 Hz, 1H), 5.00 (dt, J=7.9, 5.4 Hz, 1H), 3.46-3.23 (m, 2H), 2.32-2.09 (m, 2H), 1.61-1.54 (m, 2H), 1.51-1.19 (m, 2H), 0.90 (t, J=7.3 Hz, 3H). LC-MS (ESI), calcd for C$_{17}$H$_{22}$N$_2$O$_3$ 302.2, found m/z 303.2 (M+H$^+$).

In order to prepare N-pentanoyltryptophan from the methylpentanoyl L-tryptophanate, a NaOH (1.48 mmol) solution was added to the methylpentanoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 90% and the characteristics of the N-pentanoyltryptophan are as follows. $^1$H NMR (500 MHz, chloroform-d) δ 8.29 (s, 1H), 7.62-7.51 (m, 1H), 7.44-7.32 (m, 1H), 7.22 (ddd, J=8.2, 7.0, 1.1 Hz, 1H), 7.14 (ddd, J=8.0, 7.0, 1.0 Hz, 1H), 7.05 (d, J=2.4 Hz, 1H), 6.07 (d, J=7.7 Hz, 1H), 4.99 (dt, J=7.7, 5.4 Hz, 1H), 3.44-3.30 (m, 2H), 2.18-2.13 (m, 2H), 1.54 (p, J=7.6 Hz, 2H), 1.28 (dt, J=9.0, 7.2 Hz, 3H), 0.87 (t, J=7.3 Hz, 3H). LC-MS (ESI), calcd for C$_{16}$H$_{20}$N$_2$O$_3$ 288.2, found m/z 289.2 (M+H$^+$).

<Example 9-4> Preparation of N-undecanoyltryptophan

First, for preparation of methylundecanoyl L-tryptophanate, a mixture of undecanoic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution and then extracted 3 times with ethyl acetate. The extracted organic solvent layer was combined, washed with brine, washed with 1 N HCl, and then washed again with brine. The organic solvent layer was dried on anhydrous MgSO$_4$, concentrated, and then purified by medium-pressure liquid chromatography (MPLC) using n-hexane and ethyl acetate. The yield was 91% and the characteristics of the methylundecanoyl L-tryptophanate are as follows. $^1$H NMR (500 MHz, chloroform-d) δ 8.12 (s, 1H), 7.61-7.52 (m, 1H), 7.39 (dt, J=8.1, 0.9 Hz, 1H), 7.25-7.21 (m, 1H), 7.22-7.12 (m, 1H), 7.01 (d, J=2.4 Hz, 1H), 5.97 (d, J=7.9 Hz, 1H), 5.88-5.78 (m, 1H), 3.73 (s, 3H), 3.43-3.27 (m, 2H), 2.23-2.14 (m, 3H), 2.11-2.01 (m, 2H), 1.60 (s, 5H), 1.38 (q, J=7.0 Hz, 2H), 1.28 (d, J=2.1 Hz, 9H). LC-MS (ESI), calcd for C$_{23}$H$_{34}$N$_2$O$_3$ 386.2, found m/z 387.2 (M+H$^+$).

In order to prepare N-undecanoyltryptophan from the methylundecanoyl L-tryptophanate, a NaOH (1.48 mmol) solution was added to the methylundecanoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 88% and the characteristics of the N-undecanoyltryptophan are as follows. $^1$H NMR (500 MHz, chloroform-d) δ 8.30-8.27 (m, 1H), 7.60 (d, J=7.9 Hz, 1H), 7.38 (d, J=8.1 Hz, 1H), 7.25-7.20 (m, 1H), 7.18-7.11 (m, 1H), 7.05 (d, J=2.3 Hz, 1H), 6.06 (d, J=7.5 Hz, 1H), 5.91-5.75 (m, 1H), 5.06-4.96 (m, 2H), 3.44-3.30 (m, 2H), 2.16-2.11 (m, 2H), 2.05 (q, J=7.2 Hz, 2H), 1.54 (d, J=7.3 Hz, 2H), 1.41-1.36 (m, 2H), 1.30-1.22 (m, 11H). LC-MS (ESI), calcd for C$_{22}$H$_{32}$N$_2$O$_3$ 372.2, found m/z 373.2 (M+H$^+$).

<Example 9-5> Preparation of N-palmitoyltryptophan

First, for preparation of methylpalmitoyl L-tryptophanate, a mixture of palmitoic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution and then extracted 3 times with ethyl acetate. The extracted organic solvent layer was combined, washed with brine, washed with 1 N HCl, and then washed again with brine. The organic solvent layer was dried on anhydrous MgSO$_4$, concentrated and then purified by medium-pressure liquid chromatography (MPLC) using n-hexane and ethyl acetate. The yield was 84% and the characteristics of the methylpalmitoyl L-tryptophanate are as follows. $^1$H NMR (500 MHz, chloroform-d) δ 8.11 (s, 1H), 7.56 (d, J=7.9 Hz, 1H), 7.51-7.33 (m, 1H), 7.19-7.06 (m, 1H), 7.01 (d, J=2.4 Hz, 1H), 5.99 (d, J=8.0 Hz, 1H), 5.00 (dt, J=8.0, 5.3 Hz, 1H), 3.73 (s, 3H), 3.39-3.29 (m, 2H), 2.38 (d, J=7.5 Hz, 2H), 2.19-2.15 (m, 2H), 1.67 (d, J=7.3 Hz, 2H), 0.91 (s, 3H). LC-MS (ESI), calcd for C$_{28}$H$_{44}$N$_2$O$_3$ 456.2, found m/z 457.2 (M+H$^+$).

In order to prepare N-palmitoyltryptophan from the methylpalmitoyl L-tryptophanate, a NaOH (1.48 mmol) solution was added to the methylpalmitoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 89% and the characteristics of the N-palmitoyltryptophan are as follows. $^1$H NMR (500 MHz, chloroform-d) δ 8.19 (s, 1H), 7.60 (d, J=7.9 Hz, 1H), 7.40 (d, J=8.1 Hz, 1H), 7.27-7.21 (m, 1H), 7.18-7.12 (m, 1H), 7.08 (d, J=2.3 Hz, 1H), 4.99 (dd, J=9.2, 3.8 Hz, 1H), 3.44-3.34 (m, 2H), 2.38 (d, J=7.5 Hz, 2H), 2.14 (d, J=11.8

Hz, 2H), 1.65 (d, J=7.4 Hz, 2H), 1.28 (m, 24H), 0.91 (s, 3H). LC-MS (ESI), calcd for $C_{27}H_{42}N_2O_3$ 442.2, found m/z 443.2 (M+H$^+$).

<Example 9-6> Preparation of N—(Z)-docos-13-enoyl-L-tryptophan

First, for preparation of methyl-(Z)-docos-13-enoyl L-tryptophanate, a mixture of (Z)-docos-13-enoic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution, and then extracted 3 times with ethyl acetate. The extracted organic solvent layer was combined, washed with brine, washed with 1 N HCl, and then washed again with brine. The organic solvent layer was dried on anhydrous MgSO$_4$, concentrated, and then purified by medium-pressure liquid chromatography (MPLC) using n-hexane and ethyl acetate. The yield was 74% and the characteristics of the methyl-(Z)-docos-13-enoyl L-tryptophanate are as follows. $^1$H NMR (500 MHz, chloroform-d) δ 8.16 (s, 1H), 7.56 (dd, J=8.0, 1.1 Hz, 1H), 7.39 (dt, J=8.2, 0.9 Hz, 1H), 7.22 (ddd, J=8.2, 7.0, 1.1 Hz, 1H), 7.14 (ddd, J=7.9, 7.0, 1.0 Hz, 1H), 7.00 (d, J=2.4 Hz, 1H), 5.98 (d, J=7.9 Hz, 1H), 5.43-5.31 (m, 2H), 5.00 (dt, J=7.9, 5.3 Hz, 1H), 3.72 (s, 3H), 3.39-3.29 (m, 2H), 2.20-2.13 (m, 2H), 2.04 (q, J=6.7 Hz, 4H), 1.61 (q, J=10.0, 7.5 Hz, 2H), 1.35-1.24 (m, 28H), 0.91 (t, J=6.9 Hz, 3H). LC-MS (ESI), calcd for $C_{34}H_{54}N_2O_3$ 53/.4, found m/z 539.4 (M+H$^+$).

In order to prepare N—(Z)-docos-13-enoyltryptophan from the methyl-(Z)-docos-13-enoyl L-tryptophanate, a NaOH (1.48 mmol) solution was added to the methyl-(Z)-docos-13-enoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 92% and the characteristics of the N—(Z)-docos-13-enoyltryptophan are as follows. $^1$H NMR (500 MHz, chloroform-d) δ 8.24 (s, 1H), 7.60 (dd, J=8.0, 1.0 Hz, 1H), 7.42-7.37 (m, 1H), 7.19-7.11 (m, 1H), 7.07 (d, J=2.4 Hz, 1H), 5.38 (td, J=4.4, 2.1 Hz, 2H), 4.95 (dt, J=7.5, 5.5 Hz, 1H), 3.44-3.33 (m, 2H), 2.14 (dd, J=8.6, 6.8 Hz, 2H), 2.09-1.97 (m, 4H), 1.55 (t, J=7.4 Hz, 2H), 1.28 (dd, J=19.4, 13.4 Hz, 30H), 0.90 (t, J=6.9 Hz, 3H). LC-MS (ESI), calcd for $C_{33}H_{52}N_2O_3$ 524.4, found m/z 525.4 (M+H$^+$).

<Example 9-7> Preparation of N-stearoyl-L-tryptophan

First, for preparation of methylstearoyl L-tryptophanate, a mixture of stearoic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution, and then extracted 3 times with ethyl acetate. The extracted organic solvent layer was combined, washed with brine, washed with 1 N HCl, and then washed again with brine. The organic solvent layer was dried on anhydrous MgSO$_4$, concentrated, and then purified by medium-pressure liquid chromatography (MPLC) using n-hexane and ethyl acetate. The yield was 80% and the characteristics of the methylstearoyl L-tryptophanate are as follows. $^1$H NMR (500 MHz, chloroform-d) δ 8.09 (d, J=15.2 Hz, 1H), 7.56 (dd, J=7.9, 1.0 Hz, 1H), 7.39 (dt, J=8.2, 0.9 Hz, 1H), 7.22 (ddd, J=8.1, 7.0, 1.2 Hz, 1H), 7.14 (ddd, J=7.9, 7.0, 1.0 Hz, 1H), 7.01 (d, J=2.4 Hz, 1H), 5.00 (dt, J=7.9, 5.3 Hz, 1H), 3.73 (s, 3H), 3.39-3.28 (m, 2H), 2.37 (t, J=7.5 Hz, 2H), 2.19-2.11 (m, 2H), 1.66 (t, J=7.4 Hz, 2H), 1.59 (t, J=7.4 Hz, 2H), 0.91 (s, 3H). LC-MS (ESI), calcd for $C_{30}H_{48}N_2O_3$ 484.4, found m/z 485.4 (M+H$^+$).

In order to prepare N-stearoyltryptophan from the methylstearoyl L-tryptophanate, a NaOH (1.48 mmol) solution was added to the methylstearoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 84% and the characteristics of the N-stearoyltryptophan are as follows. $^1$H NMR (500 MHz, chloroform-d) δ 8.27-8.17 (m, 1H), 7.60 (d, J=7.9 Hz, 1H), 7.39 (d, J=8.1 Hz, 1H), 7.23 (t, J=7.6 Hz, 1H), 7.15 (t, J=7.5 Hz, 1H), 7.07 (d, J=2.2 Hz, 1H), 6.01 (d, J=7.5 Hz, 1H), 4.98 (dt, J=7.5, 5.5 Hz, 1H), 3.46-3.34 (m, 2H), 2.37 (t, J=7.5 Hz, 2H), 2.17-2.12 (m, 2H), 1.68-1.63 (m, 2H), 1.56 (t, J=7.4 Hz, 2H), 1.29 (s, 24H), 0.91 (s, 3H). LC-MS (ESI), calcd for $C_{29}H_{46}N_2O_2$ 470.4, found m/z 471.4 (M+H$^+$).

<Example 9-8> Preparation of N-oleoyl-L-tryptophan

First, for preparation of methyloleoyl L-tryptophanate, a mixture of oleic acid (2.36 mmol), L-tryptophan methyl ester hydrochloride (2.60 mmol), 1-ethyl-3-(3-dimethylaminopropyl)carbodiimide (EDCI) (2.60 mmol), hydroxybenzotriazole (HOBt) (2.60 mmol) and triethylamine (11.8 mmol) dissolved in dichloromethane was stirred at room temperature for 12 hours. The reaction mixture was concentrated, diluted with a saturated NaHCO$_3$ solution, and then extracted 3 times with ethyl acetate. The extracted organic solvent layer was combined, washed with brine, washed with 1 N HCl, and then washed again with brine. The organic solvent layer was dried on anhydrous MgSO$_4$, concentrated, and then purified by medium-pressure liquid chromatography (MPLC) using n-hexane and ethyl acetate. The yield was 73% and the characteristics of the methyloleoyl L-tryptophanate are as follows. $^1$H NMR (500 MHz, chloroform-d) δ 8.18 (s, 1H), 7.56 (dd, J=7.9, 1.0 Hz, 1H), 7.39 (dt, J=8.1, 0.9 Hz, 1H), 7.29 (s, 1H), 7.22 (ddd, J=8.2, 7.1, 1.2 Hz, 1H), 7.14 (ddd, J=8.0, 7.0, 1.0 Hz, 1H), 7.00 (d, J=2.4 Hz, 1H), 5.99 (d, J=7.9 Hz, 1H), 5.37 (qd, J=4.1, 2.1 Hz, 2H), 5.00 (dt, J=8.0, 5.3 Hz, 1H), 3.72 (s, 3H), 3.39-3.28

(m, 2H), 2.20-2.13 (m, 2H), 2.08-1.99 (m, 5H), 1.60 (t, J=7.4 Hz, 2H), 1.34-1.28 (m, 24H), 0.92-0.89 (m, 3H). LC-MS (ESI), calcd for $C_{30}H_{46}N_2O_3$ 482.4, found m/z 483.4 (M+H$^+$).

In order to prepare N-oleoyltryptophan from the methyloleoyl L-tryptophanate, a NaOH (1.48 mmol) solution was added to the methyloleoyl L-tryptophanate (0.37 mmol) dissolved in tetrahydrofuran and the mixture was stirred at room temperature for 12 hours. After adding water, the reaction mixture was extracted with dichloromethane. The aqueous layer was adjusted to pH 1 by adding 1 N HCl and then extracted 3 times with ethyl acetate. The extracted organic solvent layer was dried on anhydrous MgSO$_4$ and then concentrated. The yield was 86% and the characteristics of the N-oleoyltryptophan are as follows. $^1$H NMR (500 MHz, chloroform-d) δ 8.22 (s, 1H), 7.61 (d, J=7.9 Hz, 1H), 7.40 (dt, J=8.1, 0.9 Hz, 1H), 7.23 (ddd, J=8.1, 6.9, 1.2 Hz, 1H), 7.15 (ddd, J=8.0, 7.1, 1.0 Hz, 1H), 7.08 (d, J=2.4 Hz, 1H), 5.37 (qd, J=5.3, 4.6, 2.3 Hz, 2H), 4.95 (dt, J=7.3, 5.6 Hz, 1H), 3.45-3.33 (m, 2H), 2.17-2.10 (m, 2H), 1.59-1.51 (m, 2H), 1.38-1.26 (m, 26H), 0.91 (d, J=6.8 Hz, 3H). $C_{29}H_{44}N_2O_2$ 468.3, found m/z 469.3 (M+H$^+$).

<Example 10> Preparation of N-acetyl-γ-glutammylalanine

Figure 9:
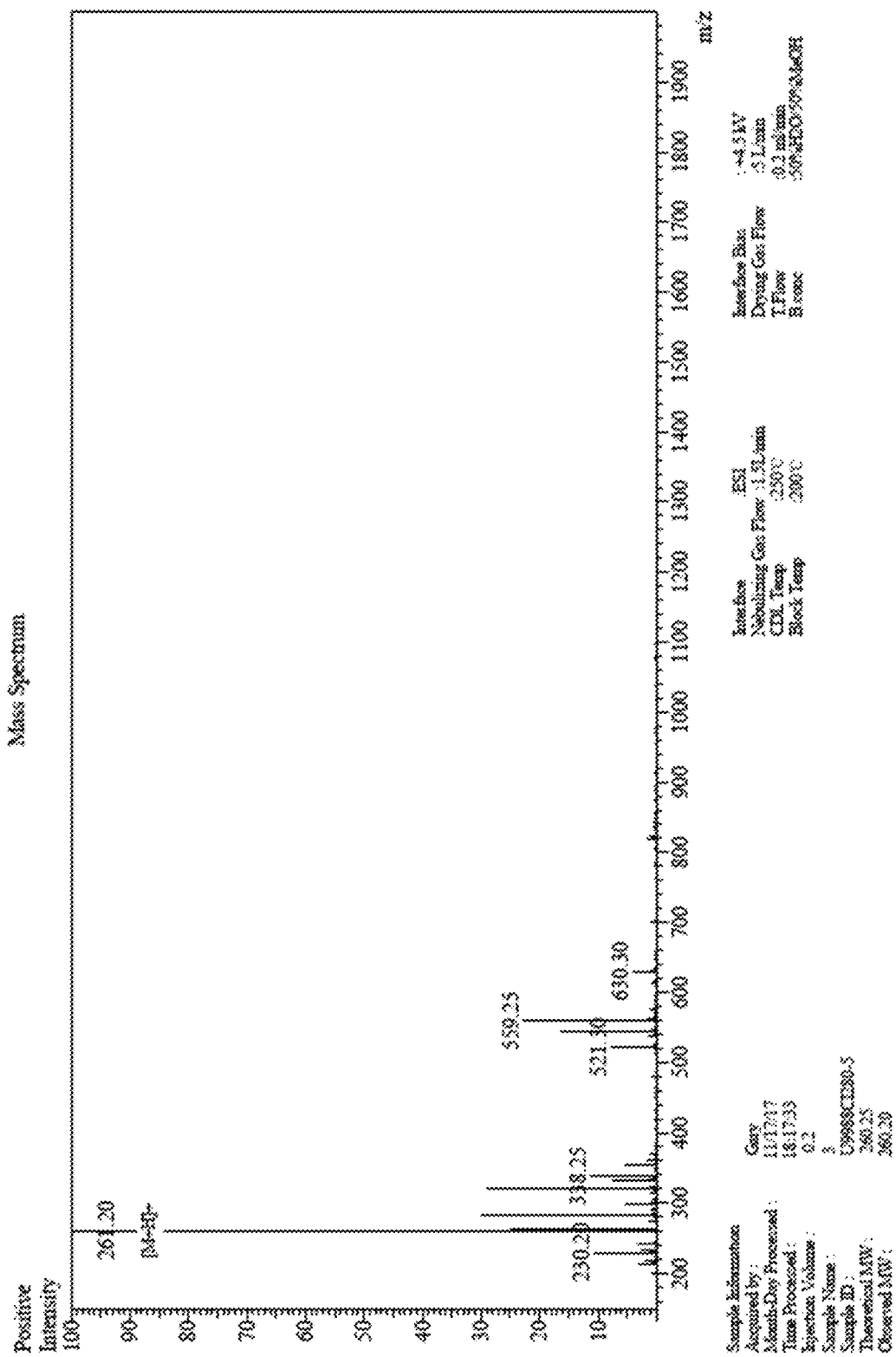
FIG. 9 shows MS data of compound N-Acetyl-γ-glutammylalanine was synthesized by Genescript (USA).

N-Acetyl-γ-glutammylalanine was synthesized by Genescript (USA). The MS data of this compound are shown in FIG. 9.

<Example 11> Evaluation of Skin-soothing Effect and Severity of Atopic Dermatitis for Acyl Derivatives of Tryptophan and Acyl Derivatives of Alanine Skin-soothing effect and the severity of dermatitis were evaluated for the acyl derivatives of tryptophan synthesized in Example 9, the acyl derivative of alanine synthesized in Example 10 and N-palmitoylalanine (purchased from Santacruz (USA)) according to the method of Example 4 (Table 2)

TABLE 2

| | Mouse 1 | | | | | | | Mouse 2 | | | | | | | Mouse 3 | | | | | | | |
|---|---|---|---|---|---|---|---|---|---|---|---|---|---|---|---|---|---|---|---|---|---|---|
| | Erythema | Edema | Eschar | Dryness | Abrasion | Licheni-fication | Sum | Erythema | Edema | Eschar | Dryness | Abrasion | Licheni-fication | Sum | Erythema | Edema | Eschar | Dryness | Abrasion | Licheni-fication | Sum | Mean | Deviation |
| Control | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| DNFB (D) | 2 | 3 | 3 | 4 | 2 | 3 | 17 | 4 | 3 | 3 | 4 | 3 | 3 | 20 | 3 | 3 | 3 | 3 | 3 | 3 | 15 | 17.3 | 2.0 |
| D + N-propionyl L-tryptophan | 2 | 2 | 2 | 2 | 2 | 2 | 12 | 2 | 2 | 2 | 3 | 2 | 2 | 13 | 2 | 1 | 2 | 1 | 2 | 1 | 9 | 11.3 | 1.7 |
| D + N-butyryl L-tryptophan | 1 | 2 | 2 | 2 | 1 | 2 | 10 | 2 | 1 | 1 | 2 | 2 | 2 | 10 | 1 | 1 | 1 | 1 | 1 | 2 | 6 | 8.7 | 1.9 |
| D + N-pentanoyl L-tryptophan | 2 | 2 | 2 | 2 | 1 | 2 | 11 | 2 | 2 | 1 | 2 | 1 | 2 | 10 | 2 | 2 | 2 | 1 | 2 | 1 | 10 | 10.3 | 0.5 |
| D + N-undecanoyl L-tryptophan | 1 | 2 | 1 | 1 | 2 | 2 | 9 | 2 | 1 | 2 | 1 | 2 | 2 | 10 | 1 | 2 | 2 | 1 | 2 | 1 | 9 | 9.3 | 0.5 |
| D + N-palmitoyl-L-tryptophan | 1 | 2 | 1 | 1 | 1 | 2 | 6 | 2 | 1 | 2 | 2 | 2 | 1 | 10 | 2 | 2 | 1 | 2 | 1 | 2 | 10 | 8.7 | 1.9 |
| D + N-(Z)-docos-13-enoyl L-tryptophan | 1 | 1 | 1 | 1 | 1 | 0 | 5 | 1 | 1 | 2 | 2 | 1 | 0 | 7 | 2 | 1 | 2 | 2 | 1 | 1 | 9 | 7 | 1.6 |
| D + N-stearyl-L-tryptophan | 2 | 2 | 2 | 2 | 2 | 2 | 12 | 2 | 2 | 1 | 2 | 2 | | | | | | | | | | | |
| D + N-oleoyl-L-tryptophan | 2 | 1 | 2 | 2 | 2 | 3 | 12 | 1 | 1 | 1 | 2 | 2 | | | | | | | | | | | |
| D + N-palmitoyl L-alanine | 1 | 2 | 1 | 1 | 1 | 1 | 7 | 2 | 1 | 1 | 1 | 1 | | | | | | | | | | | |
| D + N-acetyly-glutammyl-L-alanine | 0 | 1 | 0 | 0 | 1 | 2 | 4 | 1 | 1 | 2 | 1 | 1 | | | | | | | | | | | |

TABLE 2-continued

| | | | | | | | | | | | |
|---|---|---|---|---|---|---|---|---|---|---|---|
| D + N-stearyl-L-tryptophan | 1 | 10 | 2 | 2 | 2 | 1 | 2 | 2 | 11 | 11 | 0.8 |
| D + N-oleoyl-L-tryptophan | 3 | 10 | 2 | 1 | 1 | 2 | 2 | 2 | 10 | 10.7 | 0.9 |
| D + N-palmitoyl L-alanine | 1 | 7 | 2 | 1 | 1 | 2 | 2 | 1 | 9 | 6.7 | 0.5 |
| D + N-acetyly-glutammyl-L-alanine | 2 | 8 | 1 | 1 | 1 | 0 | 1 | 2 | 6 | 6 | 2 |

Figure 8:
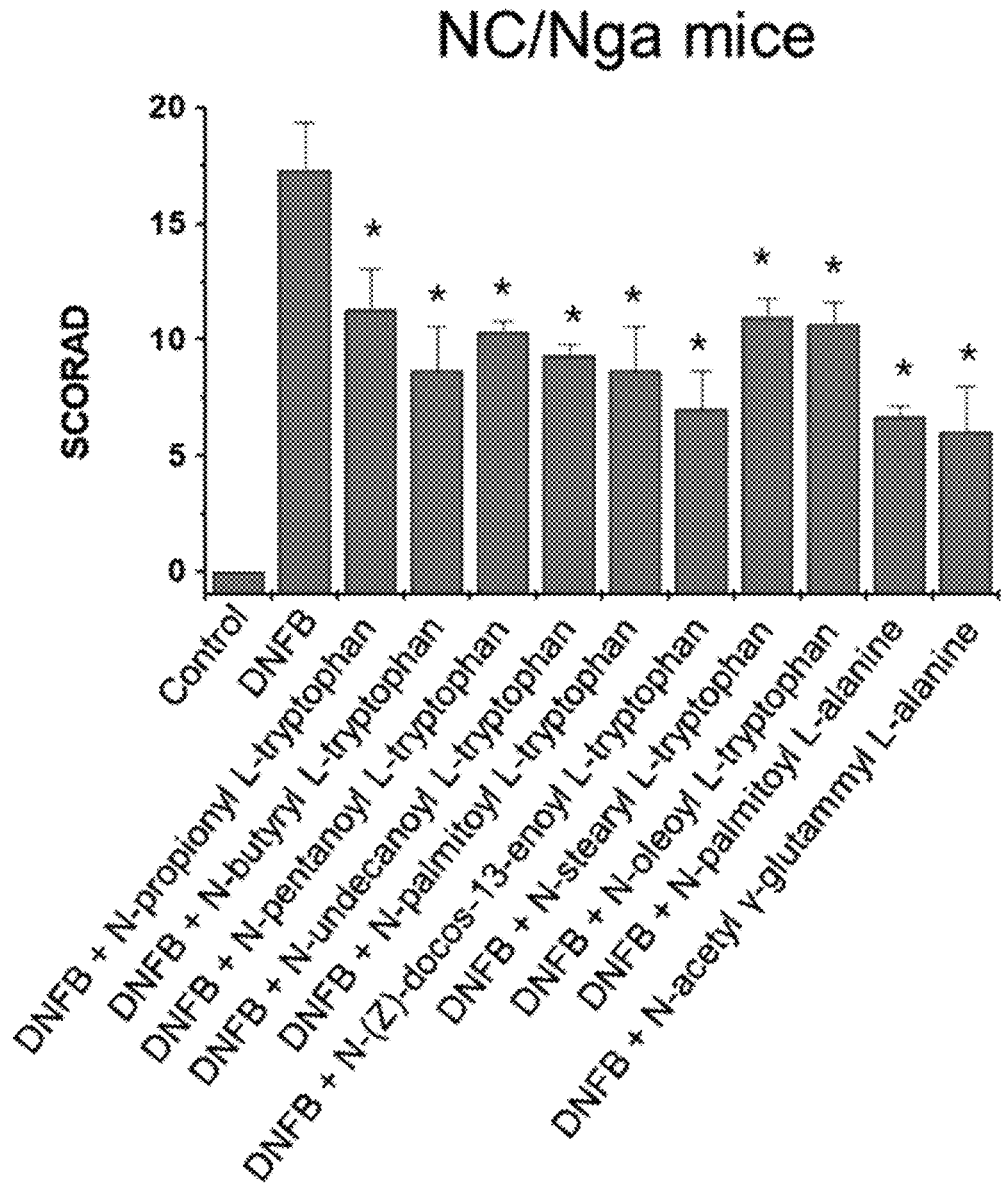
FIG. 8 shows a result of applying N-acyl-L-tryptophan, N-acetyl-γ-glutammylalanine and N-palmitoyl-L-alanine onto the dermatitis-induced area of atopic dermatitis-induced Nc/Nga mouse and then measuring clinical skin score (SCORAD) (*P<0.05 versus 2,4-dinitrofluorobenzene (DNFB)-treated group).

As seen from Table 2 and FIG. 8, N-acyl-L-tryptophan and N-acyl-L-alanine showed significant skin-soothing and atopic dermatitis-treating effects.

While the exemplary embodiments have been shown and described, it will be understood by those skilled in the art that various changes in form and details may be made thereto without departing from the spirit and scope of this disclosure as defined by the appended claims.

(Project ID) 2017R1A2A1A17069822
(Ministry in Charge) Ministry of Science and ICT
(Research Management Agency) National Research Foundation of Korea
(Research Project Title) Support of Follow-up Study of Leading Research Project
(Research Title) Development of leukotriene derivative-based candidate materials for treatment of atopic dermatitis
(Contribution Rate) 1/2
(Research Institute) Jeonbuk National University
(Research Period) 2017 Sep. 1-2019 Feb. 28
(Project ID) 2017R1A5A2015061
(Ministry in Charge) Ministry of Science and ICT
(Research Management Agency) National Research Foundation of Korea
(Research Project Title) Leading Research Center Support Project
(Research Title) Research on metabolic inflammation
(Contribution Rate) 1/2
(Research Institute) Jeonbuk National University
(Research Period) 2017 Sep. 1-2019 Feb. 28

The invention claimed is:

1. A method for decreasing expression of IL-4 and interferon γ in skin tissue in treatment of atopic dermatitis, comprising the steps of:
    a) identifying a subject having atopic dermatitis; and
    b) administering a composition to the subject, wherein said composition comprises N-acetyltryptophan or a pharmaceutically acceptable salt thereof as an active ingredient.

2. The method according to claim 1, wherein the N-acetyltryptophan is N-acetyl-L-tryptophan.

3. The method according to claim 1, wherein the composition is prepared into a formulation selected from the group consisting of a formulation for external application to skin, an aerosol, a spray, a collyrium, an oral medication, and an injection.

4. The method according to claim 1, wherein the N-acetyltryptophan consists of N-acetyl-L-tryptophan.

5. The method according to claim 1, wherein the composition further comprises a surfactant, a sterilizer, an antioxidant, a UV absorber, an anti-inflammatory agent or a cooling agent.

* * * * *